US010639367B2

(12) United States Patent
Falkenberg

(10) Patent No.: US 10,639,367 B2
(45) Date of Patent: May 5, 2020

(54) COMPOSITION COMPRISING CYTOKINE MACRO-AGGREGATES

(71) Applicant: CyTuVax, EV Maastricht (NL)

(72) Inventor: Frank Walter Falkenberg, Dortmund (DE)

(73) Assignee: CYTUVAX, Maastricht (NL)

( * ) Notice: Subject to any disclaimer, the term of this patent is extended or adjusted under 35 U.S.C. 154(b) by 0 days.

(21) Appl. No.: 14/440,413

(22) PCT Filed: Nov. 1, 2013

(86) PCT No.: PCT/EP2013/072865
§ 371 (c)(1),
(2) Date: May 4, 2015

(87) PCT Pub. No.: WO2014/068085
PCT Pub. Date: May 8, 2014

(65) Prior Publication Data
US 2015/0246115 A1    Sep. 3, 2015

(30) Foreign Application Priority Data

Nov. 2, 2012 (EP) ..................................... 12191044

(51) Int. Cl.
| A61K 39/39 | (2006.01) |
| A61K 9/14 | (2006.01) |
| A61K 9/127 | (2006.01) |
| A61K 38/19 | (2006.01) |
| A61K 9/00 | (2006.01) |
| A61K 38/20 | (2006.01) |
| A61K 38/21 | (2006.01) |
| A61K 9/16 | (2006.01) |
| A61K 39/385 | (2006.01) |
| A61K 39/00 | (2006.01) |

(52) U.S. Cl.
CPC ............ *A61K 39/39* (2013.01); *A61K 9/0019* (2013.01); *A61K 9/127* (2013.01); *A61K 9/143* (2013.01); *A61K 9/1611* (2013.01); *A61K 38/193* (2013.01); *A61K 38/208* (2013.01); *A61K 38/2013* (2013.01); *A61K 38/2026* (2013.01); *A61K 38/212* (2013.01); *A61K 39/385* (2013.01); *A61K 2039/55522* (2013.01); *A61K 2039/55533* (2013.01); *A61K 2039/585* (2013.01); *A61K 2039/622* (2013.01)

(58) Field of Classification Search
None
See application file for complete search history.

(56) References Cited

U.S. PATENT DOCUMENTS

| 4,604,377 | A | * | 8/1986 | Fernandes | ............ | A61K 9/0019 424/278.1 |
| 4,962,091 | A | * | 10/1990 | Eppstein | ............. | A61K 9/1647 424/130.1 |
| 5,409,698 | A | * | 4/1995 | Anderson | ............... | A61K 9/127 424/283.1 |
| 6,514,533 | B1 | * | 2/2003 | Burke | .................. | A61K 9/0019 424/457 |
| 6,544,549 | B1 | * | 4/2003 | Boni | ..................... | A61K 9/1277 264/4.1 |
| 2002/0039571 | A1 | * | 4/2002 | Falkenberg | ........ | A61K 39/0011 424/93.1 |
| 2002/0176845 | A1 | * | 11/2002 | Falkenberg | ........ | A61K 39/0011 424/85.1 |
| 2007/0110771 | A1 | * | 5/2007 | Good | ................... | A61K 39/015 424/272.1 |

(Continued)

FOREIGN PATENT DOCUMENTS

| EP | 1688146 A1 | * | 8/2006 | ............. | A61K 47/20 |
| EP | 1688146 A1 | | 8/2006 | | |
| WO | WO-9101143 A1 | * | 2/1991 | ............. | A61K 39/39 |

OTHER PUBLICATIONS

Chang, B.S. and Hershenson, S. 2002. Practical approaches to protein formulation development in "Rationale Design of stable protein formulations-theory and practice" (J.F. Carpenter and M.C. Manning eds.) Kluwer Academic/Plenum publishers, New York. pp. 1-25.*
Teller et al. (Correction of genetically determined low and non-responsiveness to Hepatitis B surface antigen by vaccination with a mixture of alum-adsorbed HBsAg and alum-adsorbed cytokines. Abstract. Immunopotentiators in modern vaccines. IMV 2002 Abstracts, May 14-16, 2002, Radisson SAS Hotel, Prague, Czech Republic).*
Fatima et al. Insufficient (Sub-native) Helix Content in Soluble/Solid Aggregates of Recombinant and Engineered Forms of IL-2 Throws Light on How Aggregated IL-2 is Biologically Active. Protein J., 2012; 31:529-543.*

(Continued)

*Primary Examiner* — Vanessa L. Ford
*Assistant Examiner* — Sandra E Dillahunt
(74) *Attorney, Agent, or Firm* — McDonnell Boehnen Hulbert & Berghoff LLP

(57) ABSTRACT

The present invention provides methods and compositions for the stimulation of immune responses. In particular, the present invention provides compositions (e.g., vaccines) and methods of using the same for the induction of immune responses (e.g., innate and adaptive immune responses (e.g., for generation of host immunity against cancer (e.g., a tumor) or against any type of antigen (e.g. bacterial, viral, parasite-derived)). Compositions and methods of the present invention find use in, among other things, clinical (e.g. prophylactic, therapeutic and preventive medicine (e.g., vaccination)) and research applications. It particularly relates to the area of active specific immunotherapy of cancer ("cancer vaccines"), and provides procedures for the preparation of therapeutic vaccines that can eliminate cancer cells. These vaccines are constructed in such a way that they mimic the release and exchange of cytokines and other bio-molecules on the local cellular level as they occur during induction of natural immune responses.

16 Claims, 13 Drawing Sheets

(56) References Cited

U.S. PATENT DOCUMENTS

Figure 1A:
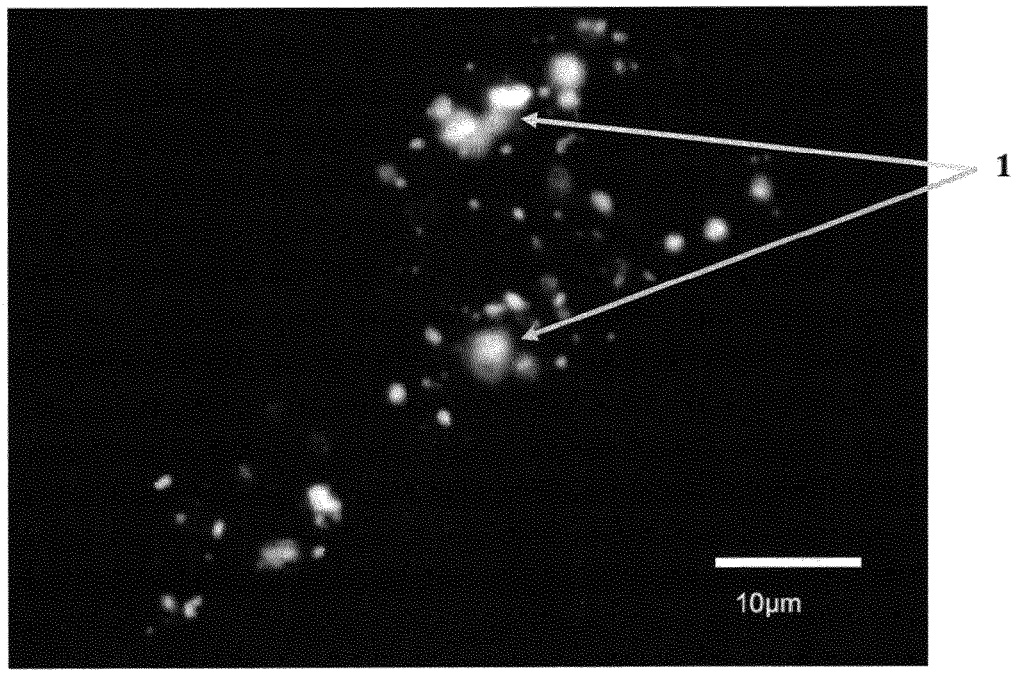

2009/0226530 A1* 9/2009 Lassner ............... A61K 9/1605
514/1.1

OTHER PUBLICATIONS

Mandal et al. Immobilization of GM-CSF onto particulate vaccine carrier systems. International Journal of Pharmaceutics, 2004; 269:259-265 (Year: 2004).*

Argiro et al. Induction of a protective immunity against Schistosoma mansoni with ovalbumin-coupled SM37-5 coadsorbed with GM-CSF or IL-12 on alum. Vaccine, 1999; 17:13-18 (Year: 1999).*

Fatima et al. Insufficient (Sub-native) helix content in soluble/solid aggregates of recombinant and engineered forms of IL-2 throws light on how aggregated IL-2 is biologically active. Protein J., 2012; 31:529-543 (Year: 2012).*

Chang, B.S. and Hershenson, S. 2002. Practical approaches to protein formulation development in "Rationale Design of stable protein formulations-theory and practice" (J.F. Carpenter and M.C. Manning eds.) Kluwer Academic/Plenum publishers, New York. 1-25 (Year: 2002).*

International Preliminary Report on Patentability completed Jul. 10, 2014 pertaining to International Application No. PCT/EP2013/072865.

European Search Report completed Mar. 7, 2013 pertaining to European Patent Application No. 12191044.2.

International Search Report and Written Opinion completed Jan. 15, 2014 pertaining to International Application No. PCT/EP2013/072865.

Sofia Grille et al., "A B-cell lymphoma vaccine using a depot formulation of interleukin-2 induces potent antitumor immunity despite increased numbers of intratumoral regulatory T cells", Cancer Immunology, Immunotheraty, Springer, Berlin, DE, vol. 59, No. 4, Sep. 19, 2009, pp. 519-527, XP019778763, ISSN: 1432-0851.

* cited by examiner t = 3h t = 4h

COMPOSITION COMPRISING CYTOKINE MACRO-AGGREGATES

FIELD OF THE INVENTION

The present invention provides methods and compositions for the stimulation of immune responses. In particular, the present invention provides compositions (e.g., vaccines) and methods of using the same for the induction of immune responses (e.g., innate and adaptive immune responses (e.g., for generation of host immunity against cancer (e.g., a tumor) or against any type of antigen (e.g. bacterial, viral, parasite-derived)). Compositions and methods of the present invention find use in, among other things, clinical (e.g. prophylactic, therapeutic and preventive medicine (e.g., vaccination)) and research applications.

It particularly relates to the area of active specific immunotherapy of cancer ("cancer vaccines"), and provides procedures for the preparation of therapeutic vaccines that can eliminate cancer cells. It further relates to the area of immunization against pathogens.

These vaccines are constructed in such a way that they mimic the release and exchange of cytokines and other bio-molecules between cells on the local cellular level as they occur during induction of natural immune responses.

BACKGROUND TO THE INVENTION

Vaccination is an extremely complex process, which mimics molecular and cellular processes occurring during induction of natural immune responses after injury and microbiological infections and which involves two strictly local reactions: one at the level of the inoculation site and one on the level of the draining lymph node(s).

In such natural immune responses, interactions between cells of the immune system are regulated and directed by the exchange of cytokines in the cytokine network. Most of our knowledge about the interactions between the cells of the immune system and about the actions of cytokines in these interactions has been elaborated by in vitro experimentation. Based on said results it is generally accepted that many types of cells of the innate and the adaptive immune system are "professional" secretors.

They have the intracellular machinery to produce, store and release a variety of cytokines, chemokines and other secreted substances (mediators, e.g. Serotonin, Histamine).

Results of recent research (Huse, Morgan, B. F. Lillemeier. M. S. Kuhns, D. S. Chen & M. M. Davis) show that T cells use two directionally distinct pathways for cytokine secretion. 2006 Nature Immunology 7, 247-255; Stanley, C. Amanda and Lacy Paige Pathways for Cytokine secretion. 2010. Reviews. Physiology 25, 218-229) have shown that the cytokine molecules can be released either by exocytosis to the outside of the cells or directed to synapses through which cells are in contact with each other, e.g. to the immunological synapses between T lymphocytes and antigen presenting cells, or through multi-directional pathways (e.g. by constitutive cytokine release by carrier vesicles that transport cargo to the plasma membrane for immediate (within minutes of stimulation) release, or by piecemeal degranulation of small secretory vesicles), or by directed bimodal secretion (the release of different cargo (=cytokines) in different directions) enables cells to engage simultaneously in both "public" (to all the cells in proximity) and "private" (to a cell in contact) intercellular "conversation".

Consequently, cytokine concentrations at the site of injury or inflammation will be dependent;

on the momentary position of the cells in relation to each other;

on the activation/stimulation state of the cells involved;

on the way the cytokine molecules are released (timing, trickle or burst); and on the mobility of released cytokine molecules in the extra-cellular fluid (speed of diffusion, concentration gradient, distance the molecules can migrate).

Present pharmacology has not yet found ways and procedures to interact and mimic these inter-cellular processes of the immune system at the local cellular level. So far practically all pharmaceutical interactions are based on systemic (i.v., s.c., i.d.) applications. However, if molecular messenger molecules, such as cytokines, are applied systemically, they tend to flood the organism and actually render local cell-to-cell interactions impossible. Nevertheless, in specific circumstances, they can induce and modify immune reactions, e.g. in the treatment of cancer by activation of lymphocytes that have infiltrated tumor lesions or metastases (TIL: Tumor-Infiltrating Lymphocytes) and have been rendered inert by the tumor cells.

Cells of the immune system are capable of producing, storing and releasing more than a single cytokine. It can further be assumed that each cytokine is released for a different purpose. Thus, it is rather unlikely that all the cytokines are stored in the same vesicles and always released together. This has also been shown experimentally. The mechanisms of this finely tuned molecular machinery that regulates secretion of dozens of cytokines, chemokines and other small molecule mediators (e.g. by mast cells) is not understood today but must be responsible for the release processes.

Cytokine molecules are released when a cytokine-containing vesicle fuses with the cell's membrane and opens to the outside or through a synapse into another cell. Such a process cannot result in a slow continuous flow of cytokine molecules from the cell to its outside, but has to be burst-like, "shooting" the cytokine molecules into the extra-cellular environment or through a synapse into a neighboring cell.

In the vesicles, the cytokine molecules are densely packed. Consequently near the point of release, close to the surface of the cells, cytokine concentrations are extremely high. But after a few cell diameters of diffusion they will be reduced to concentrations required for binding to cytokine receptors. Some of the cytokine molecules might reach the vascular system; most will just be lost in the extra-cellular space.

In 1996 David R. Kaplan published a review (Kaplan, David R. Autocrine secretion and the physiological concentration of cytokines. 1996 Trends. Immunology Today 17, 303-304), in which he has summarized data from other researchers. Based on these data he has made the following estimate:

1. a single activated T lymphocytes is capable of releasing about 0.04 pg of IL-2 per hour, corresponding to about $10^6$ IL-2 molecules.
2. these 0.04 pg of IL-2 are stored in 20-2,000 vesicles in extremely high density of 1-100 mM (corresponding to 12-1.200 gram of IL-2 per litre).
3. after fusion of a cytokine-containing vesicle with the cell's membrane and opening of the vesicle to the outside of the cells, IL-2 concentration will be in the same range of 1-100 mM.

4. This concentration is much too high for binding to the T cell receptor on the same cell's membrane.
5. after diffusion during about 100 seconds and in a few cell diameters distance from the secreting lymphocyte, IL-2 concentration reaches the level required for binding to cytokine receptors.

Consequently, in an immune reaction, each activated T cell would burst-out a shower of about 1,000,000 IL-2 molecules released from between 20 and 2,000 vesicles of different sizes (=between 500-50,000 Molecules per vesicle)

In order to imitate such a reactions, it is not sufficient to release a trickle of IL-2 molecules, as is the case with cytokine gene-transfected tumor cells, as they have been applied in cancer vaccines (e.g. Nemunaitis et al. J. Natl. Cancer Inst. (2004) 96:326-331).

Also the local injection of several hundred micrograms of cytokines as is done in systemic cytokine treatment is far away from the natural process: a huge shower of trillions (more than 1,000,000,000,000) of cytokine molecules is not capable of imitating the natural release pattern of a professional secretory cell.

The local release of such a huge amount of cytokine molecules, corresponding to the simultaneous release by several millions of activated lymphocytes, will never happen under natural conditions and will cause absolute chaos at and around the inoculation site and—after reaching the vascular system—might also cause havoc in distant locations.

Direct application of IL-2 under the trade name Proleukin (Chiron Corp.) has been approved by the United States FDA for the treatment of adults with metastatic renal cell carcinoma and metastatic melanoma. Already from the early stages of research into IL-2 containing pharmaceutical compositions, it was apparent that aggregation-preventing agents are needed to ensure solubility of IL-2. For example, in U.S. Pat. No. 4,604,377, which describes the earliest pharmaceutical compositions of IL-2, indicates that about 100 to about 250 µg sodium dodecyl sulfate (SDS) should be present to avoid IL-2 aggregation and ensure solubility.

EP1688146, which describes amongst others the process to obtain the Proleukin composition, further details the importance of the amount of SDS in the composition. The needed amount of SDS is considered to be 95 to 250 µg per mg of IL-2, at which concentration the IL-2 is present in microaggregates of approximately 25-60 IL-2 molecules per aggregate. The preferred amount of SDS is, as also present in the Proleukin formulation, 160 µg SDS per mg IL-2, which leads to microaggregates of about 27 molecules IL-2, with a diameter of about 12 nm. As the SDS concentration drops below 95 µg/mg, the sizes of the aggregates rise sharply, leading to worse in vivo pharmacokinetics. The clearance rate in rats was even found to be 30-fold higher for a composition containing 25 µg SDS per mg IL-2 compared to the preferred composition of 160 µg SDS per mg IL-2.

An interesting variation of direct injection of IL-2 such as injection of Proleukin, is presented in U.S. Pat. No. 6,406,689. In that patent, the aforementioned Proleukin IL-2 formulation (comprising SDS in a range of 95 to 250 µg per mg) is adsorbed to aluminum hydroxide. Thereafter, it is mixed with irradiated tumor cells and injected into mice wherein renal carcinoma was induced. While survival rates where higher for IL-2 in combination with irradiated tumor cells compared to irradiated tumor cells alone, survival rates further increased when IL-2 was adsorbed to aluminum hydroxide.

The inventor of the present invention has surprisingly found that generating cytokine macro-aggregates of e.g. IL-2 and adsorbing these to a depot material, such as aluminum hydroxide, leads to compositions with improved pharmaceutical properties. Instead of the expected worse in vivo pharmacokinetics associated with these systemically applied macro-aggregates as described in EP1688146, these macro-aggregates actually improve in vivo outcome compared to micro-aggregates, when adsorbed to a depot material and applied as adjuvants in vaccines, as will be described hereinafter.

It has thus been an object of the present invention to provide an improved composition for inducing immune responses, in particular for treating tumors, such as for vaccination against cancer.

Further to the surprise of the inventor, such a composition comprising cytokine macroaggregates adsorbed to a depot material and antigenic material appears to closely mimic the natural immune system. As will be described in more detail hereinafter, it has been found that cytokine molecules or small aggregates are released from the macro-aggregates in localized bursts, similar to the vesicle release observed in the secretory events of cells of the immune system. Furthermore, said vaccine formulation is being characterized in participating in immune-stimulatory processes not only locally at the inoculation site, but also in the lymph node(s) draining the area of the inoculation site. Without wishing to be bound by theory, it is currently assumed that the CD25A receptor might play a role in this effect. Mature CD86+ dendritic cells bear the low affinity CD25A IL-2 receptor. Due to its low affinity properties the CD25A low affinity receptor on the CD86+ dendritic cells binds IL-2 aggregates rather than isolated IL-2 molecules. This might be the reason that the CD86+ dendritic cells carry both, antigenic fragments and IL-2 aggregates, to the lymph nodes.

Thus, it is also an object of the present invention to provide the use of a composition comprising such cytokine macroaggregates in mimicking the natural immune system and stimulating it, not only at the inoculation site, but also at the lymph node(s) draining the area of the inoculation site.

BRIEF DESCRIPTION OF THE DRAWINGS

With specific reference now to the figures in detail, it is stressed that the particulars shown are by way of example and for purposes of illustrative discussion of the different embodiments of the present invention only, and are presented in the cause of providing what is believed to be the most useful and readily description of the principles and conceptual aspects of the invention. In this regard no attempt is made to show structural details of the invention in more detail than is necessary for a fundamental understanding of the invention, the description taken with the drawings making apparent to those skilled in the art how the several forms of the invention may be embodied in practice.

FIG. 1. Detailed views of composition of the invention consisting of IL-2 macro-aggregates adsorbed to alum particles

1*a*. Composition of the invention comprising IL-2 macro-aggregates adsorbed to alum. IL-2 is identified by incubation with a monoclonal IgG antibody specific for human IL-2 followed by incubation with an AlexaFluor 488 labeled Goat anti mouse IgG (h&I) antibody. Macro-aggregates of IL-2 can be recognized in dot-like locations (1) on a large lump of alum.

The large alum aggregate shown in this picture has a size of about 20×60 μm. The size of the dot-like IL-2 aggregates on the alum matrix can be estimated to be between 50 nm and 6000 nm. Similar observations were made for macro-aggregated IL-2 adsorbed to latex beads.

1b. Composition of the invention. IL-2 was stained green, alum was stained red. After grey-scale conversion as in FIG. 1b, IL-2 is shown in a lighter shade of grey than alum. The picture shows a laser scanning microscopy picture of a detail of an alum particle (2) with IL-2 macro-aggregates (1) adsorbed thereto. Some small IL-2 macro-aggregates (3) that are adsorbed to the alum particle can also be seen.

Figure 2:
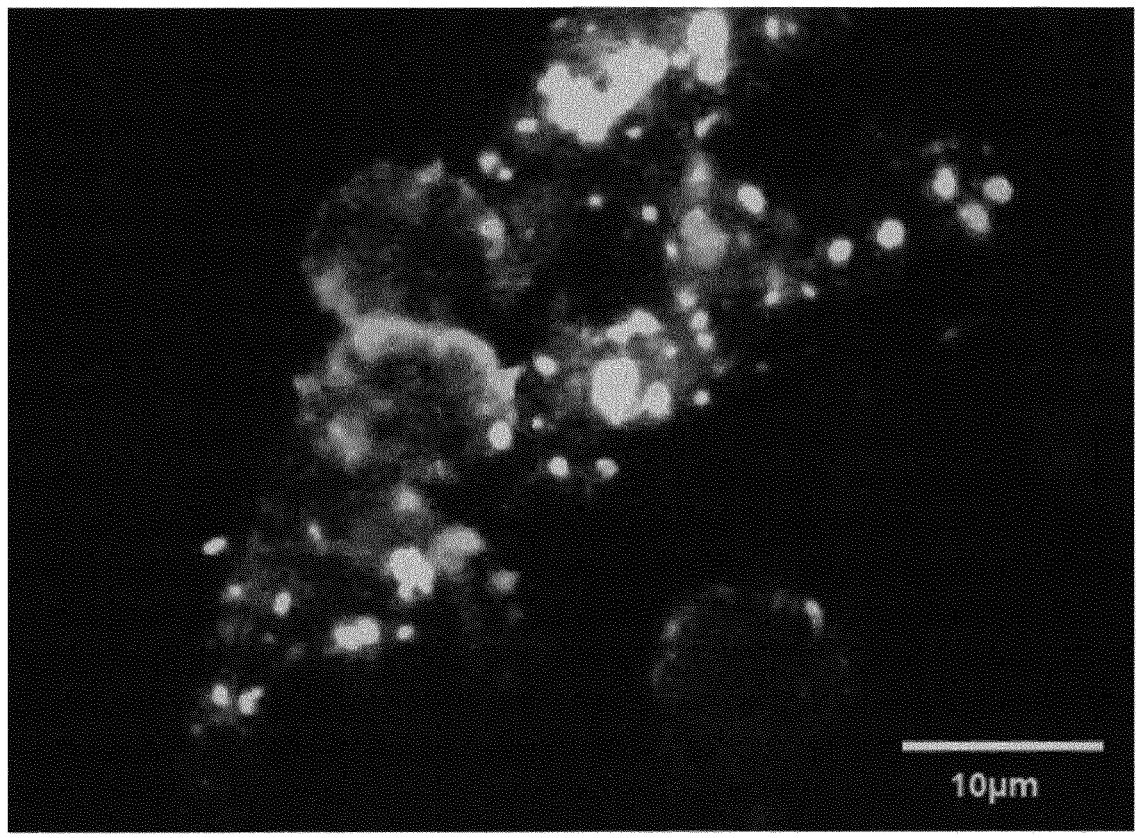

FIG. 2. Cancer Vaccine Formulation according to the present invention. Alum particles loaded with IL-2 macro-aggregates (2) and Texas Red labeled tumor cells (1). IL-2 was identified by incubation with a monoclonal IgG antibody specific for human IL-2, followed by incubation with an AlexaFluor 488 labeled Goat anti mouse IgG (h&l) antibody.

Macro-aggregates of IL-2 can be recognized in dot-like locations (2) on a large lump of alum. Tumor cells and tumor cell fragments (1) are identified by the red fluorescence of the Texas Red labeled tumor cells.

Figure 3:
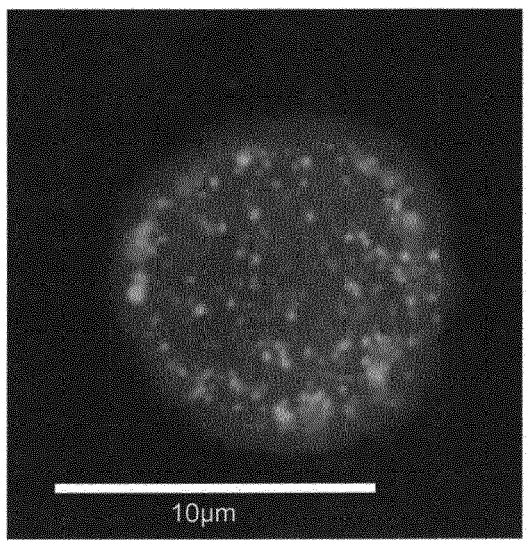

FIG. 3. Cancer Vaccine Formulation according to the present invention. Irradiated B16 murine melanoma cells loaded with macro-aggregates of IL-2. Cell-bound IL-2 was identified using an IL-2 specific IgG antibody, followed by incubation with a Fluorescein-labeled goat anti mouse IgG antibody.

Figure 4A:
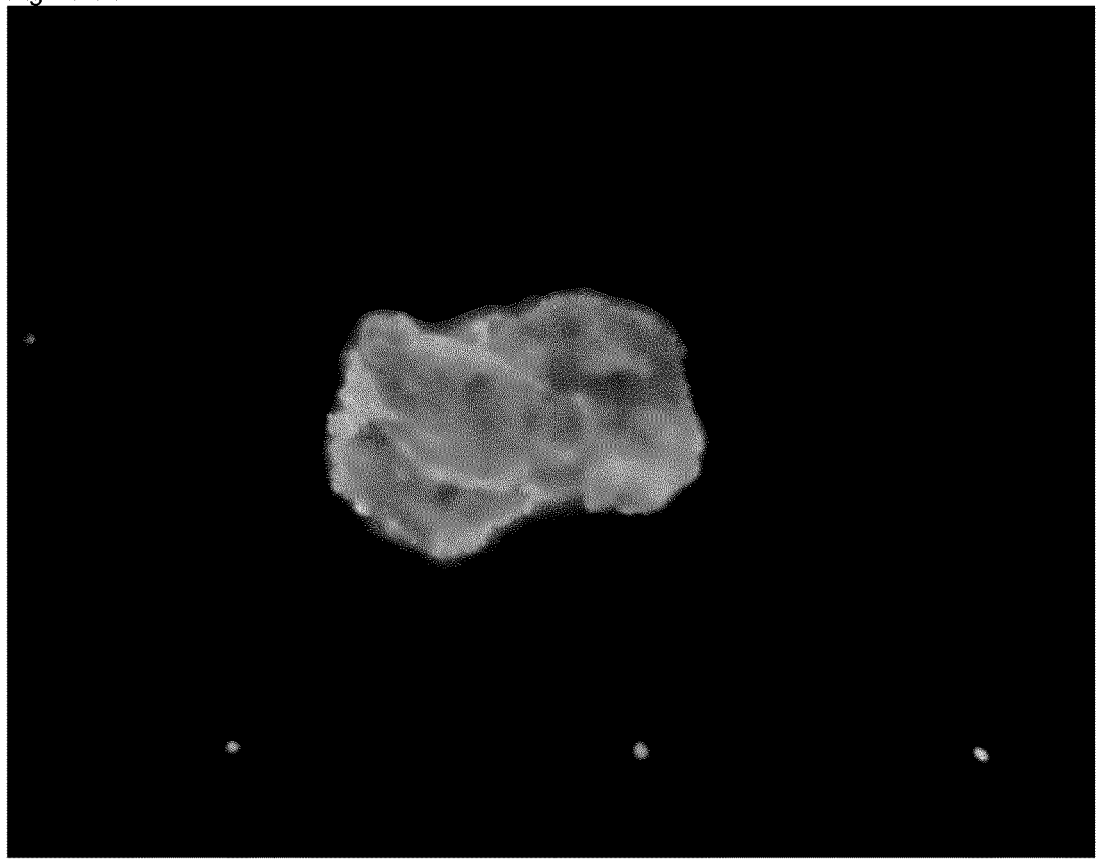
Figure 4B:
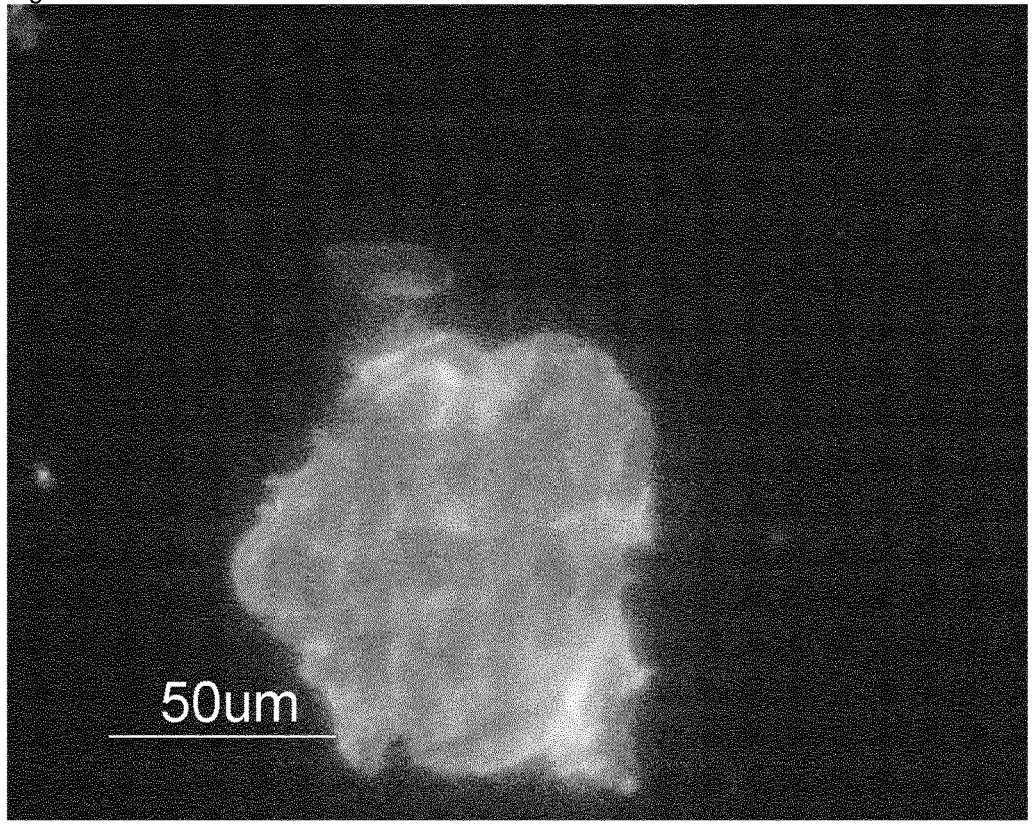

FIG. 4. Compositions prepared without cytokine macro-aggregate formation
   4a. Alum particle with IL-2 prepared using an SDS-containing buffer instead of the formulation of the present invention.
   4b. Alum particle prepared according to US20020176845. Compared to the alum particle shown in FIG. 1, the IL-2 that is identified by incubation with a monoclonal IgG antibody specific for human IL-2 followed by incubation with an AlexaFluor 488 labeled Goat anti mouse IgG (h&l) antibody, is homogenously distributed on the alum particle in FIGS. 4a and 4b.

Figure 5:
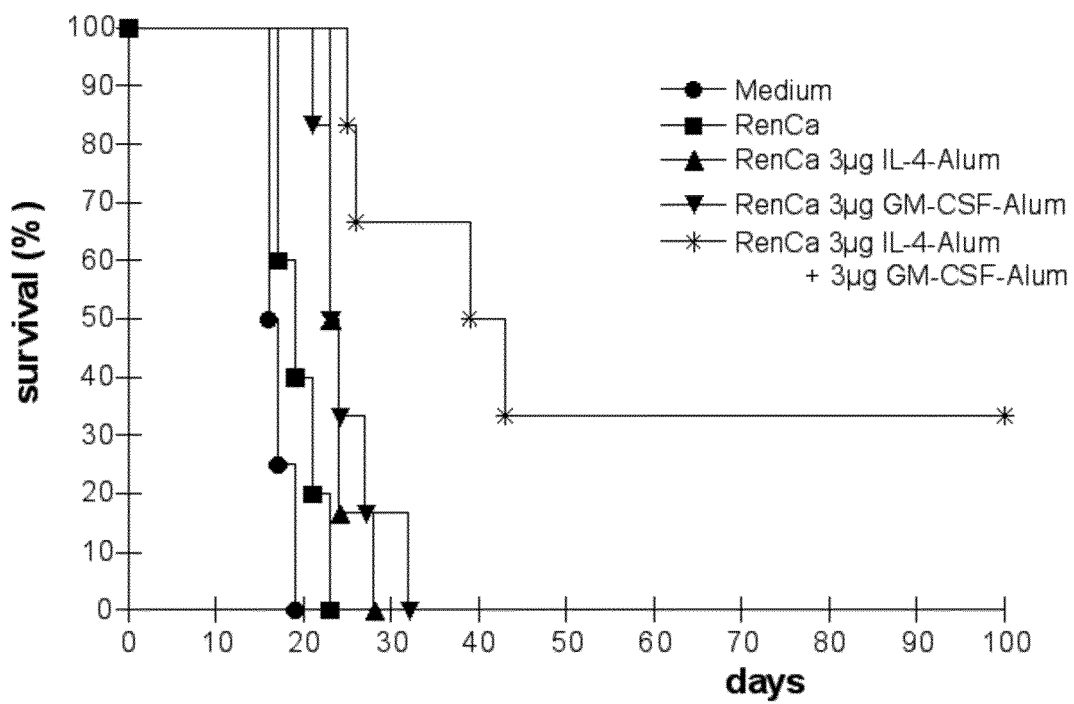

FIG. 5. Synergistic effect of macro-aggregated GM-CSF and IL-4 in RenCa therapeutic vaccination. Survival plot for a RenCa therapeutic vaccination study with a subcutaneous administration with irradiated tumour cells and different macro-aggregated cytokine depot preparations, i.e. recombinant murine GM-CSF (rmuGM-CSF), rmuIL-4 and the combination thereof.

FIG. 6a-f. Photographs of tissue slices prepared from the inoculation sites of vaccine preparations applied to mice. The photographs were converted to grey-scale for this patent application, thereby rendering the red and green visualizations grey.
   6a A control vaccine preparation containing, as a tracer, a small dose of Texas Red labelled bovine serum albumin attached to aluminum hydroxide ("alum"). Alum-adsorbed macro-aggregated cytokines were not added to the vaccine preparation. Tissue slices (7 μm) were prepared from shock-frozen material excised from the inoculation site 11 days after vaccination and incubated with monoclonal rat antibody specific for murine endothelial cells (anti-CD31), followed by incubation with an AlexaFluor 488 labeled donkey anti rat IgG (h&l) antibody. The red fluorescent stain (1) identifies the inoculated material; the green fluorescent stain (2) shows the presence of capillaries in the normal skin tissue of the mouse. No capillaries are seen in and around the inoculum.
   6b A mouse was injected with a composition according to the invention containing irradiated murine tumour cells and Texas Red labeled bovine serum albumin attached to aluminum hydroxide and
      10 μg alum adsorbed macro-aggregated recombinant human IL-2
      2 μg alum adsorbed macro-aggregated recombinant murine IL-4
      3 μg alum adsorbed macro-aggregated recombinant human Interferon alpha
      3 μg alum adsorbed macro-aggregated recombinant murine GM-SCF Tissue slices (7 μm) were prepared from shock-frozen material obtained from the inoculation site 11 days after vaccination and incubated with monoclonal rat antibody specific for murine endothelial cells (anti-CD31), followed by incubation with an AlexaFluor 488 labeled donkey anti rat IgG (h&l) antibody.

The red fluorescent stain (1) identifies the inoculated material, the green fluorescent stain (2) shows the sprouting of capillaries in and around the inoculum.
   6c The same composition as in 6b above. Tissue slices (7 μm) were prepared from shock-frozen tissue material obtained from the inoculation site 19 days after vaccination and incubated with a monoclonal rat antibody specific for murine reticular fibroblasts (ER-TR7), followed by incubation with an AlexaFluor 488 labeled donkey anti rat IgG (h&l) antibody.

The red fluorescent stain (1) identifies the inoculated material, the green fluorescent stain (2) shows the capsule formed by fibroblasts around the inoculum.
   6d The same composition as in 6b-c above. Tissue slices (7 μm) were prepared from shock-frozen tissue material obtained from the inoculation site 19 days after vaccination and incubated with a monoclonal rat antibody specific for murine CD4 T-cells (H129.19), followed by incubation with an AlexaFluor 488 labeled donkey anti rat IgG (h&l) antibody.

The red fluorescent stain (1) identifies the inoculated material, the green fluorescent stain (2) shows CD4 helper T cells invading the capsule and the inoculum.
   6e A mouse was injected with a composition of the invention comprising irradiated tumor cells and IL-2 macro-aggregates adsorbed to alum particles. 24 hours after injection, tissue slices from the inoculum site were prepared and stained (IL-2: green, tumor cells: red). The image was converted to grey-scale and inverted, rendering stained material dark grey or black. The inoculum (1) is shown black due to the abundant presence of tumor cells and IL-2 from the vaccine composition. The whole area surrounding the inoculum site is swarmed by macro-aggregated IL-2, shown as black spots, some of which are indicated by arrows (2). A dendritic cell (3) can be seen that binds tumor fragments (4) and IL-2 aggregates (2).
   6f Tissue slices from the lymph node that drains the inoculum site were prepared from the mouse as described in 6e. IL-2 macro-aggregates transported to the lymph node can be seen in the intercellular space (white spots).

Figure 7A:
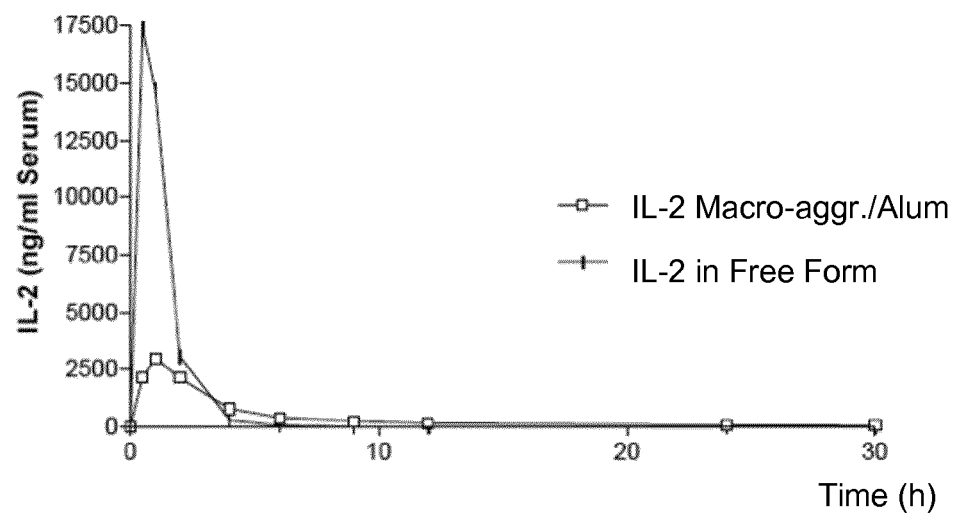
Figure 7B:
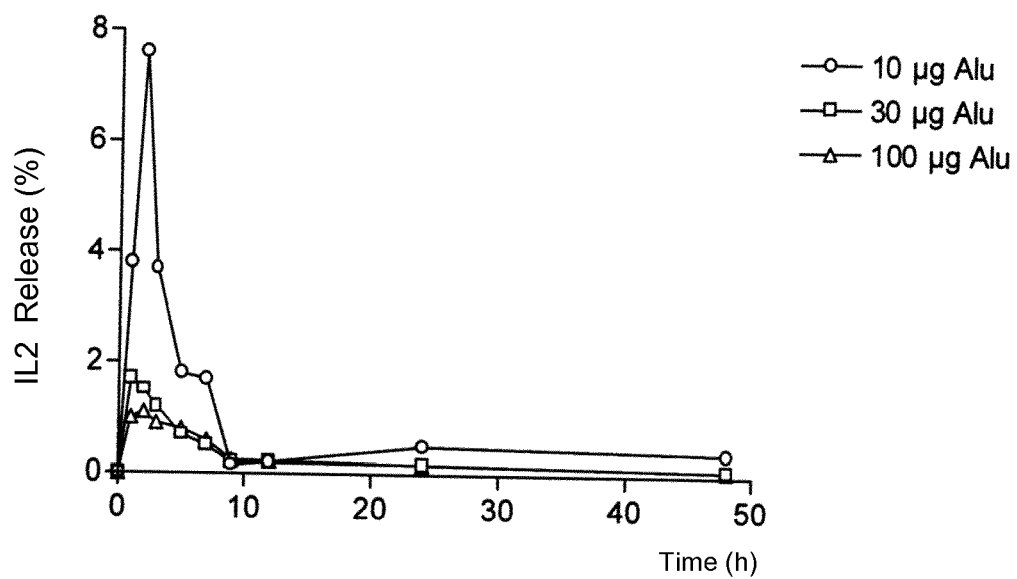

FIG. 7. A In vivo release of IL-2 from subcutaneously injected IL-2 macro-aggregates adsorbed on Alum depot and of subcutaneously injected free IL-2. The free IL-2 shows a high release peak of about 1.750 ng and drops to zero after about 6 hours. The alum-adsorbed IL-2 macro-aggregates show a lower peak of about 250 ng, followed by a slow release in the 50-100 ng range till after about 30 hours. B In vitro release of IL-2 from IL-2 macro-aggregates adsorbed on Alum depot., 10 μg of macro-aggregated IL-2 were adsorbed on 10 μg, 30 μg and 100 μg of Alum, respectively. Shows again the initial peak followed by a sustained release of about 50 ng/24 hours, with an optimum for saturated loading of the alum. As can be seen from this figure, underloading of the cytokine to the depot (30 μg and 100 μg of Alum) has an overall negative effect on IL-2 release from the depot.

Figure 8:
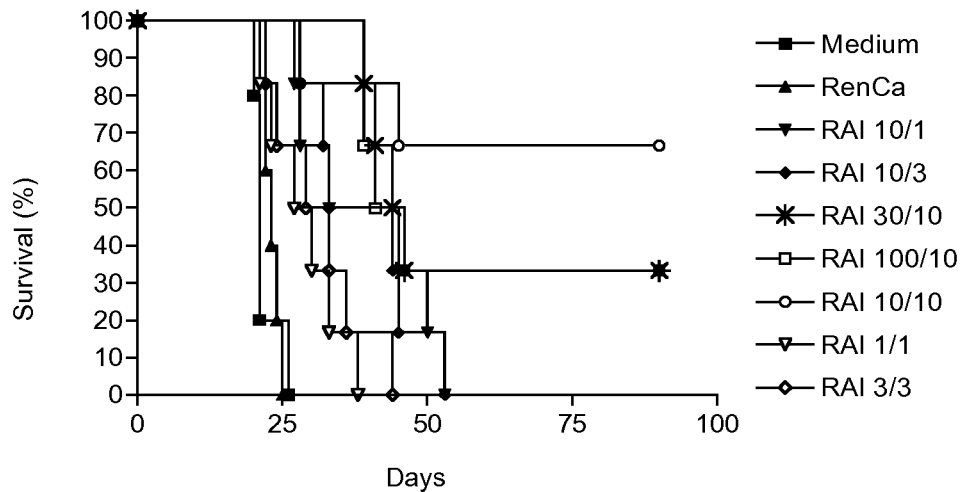

FIG. 8. Survival plot for a RenCa therapeutic vaccination study with a subcutaneous administration with different IL-2 macro-aggregate loading of the alum depot. The first number gives the amount of alum, the second the amount of macro-aggregated cytokine. It thus appears that for alum/IL-2 an optimum exists from 10/10 to 30/10. If IL-2 is adsorbed to an excess of alum, like with 100/10, this has a negative effect on the observed survivals.

Figure 9:
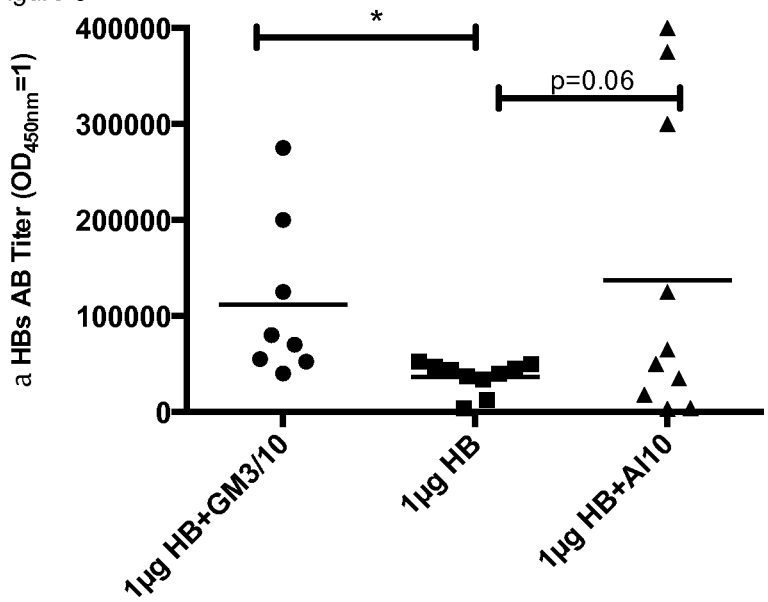

FIG. 9. Significant enhancement of HBsAg antibody titres in mice vaccinated by injection of a commercially available Hepatitis B vaccine (e.g. Recombivax HB) additionally adjuvanted by alum-attached cytokines (IL-2, GM-CSF).

For this investigation the commercially available Recombivax HB vaccine (40 μg of HBsAg adsorbed to an alum compound in an injectable dose of 1.0 ml) was used. ¹⁄₄₀ of the human dose was chosen as a dose suitable for vaccination of mice. 50 μl of the human dose (equaling 1.0 μg of HBsAg) were mixed with 50 μl of alum-attached IL-2 (10 μg of rhuIL-2 attached to 10 μg alum) or alum-attached GM-CSF (3.0 μg of rmuGM-CSF attached to 10 μg of alum) and applied intra-muscularly to the muscle of the hind leg of the mouse. Blood was collected 15 days after a single injection.

IgG Antibody titres were determined in an ELISA with solid phase attached recombinant HBsAg (Serum Institute of India).

It is clear from the figure that the addition of either of the 2 cytokine-adjuvants, alum attached IL-2 ("Al10") and alum-attached GM-CSF ("GM3/10"), to the Recombivax HB vaccine results in significantly enhanced antibody titres. The antibody titres induced by alum-attached GM-CSF are considerably higher than the antibody titres induced by alum-attached IL-2 as adjuvant (p=0.06).

Figure 10:
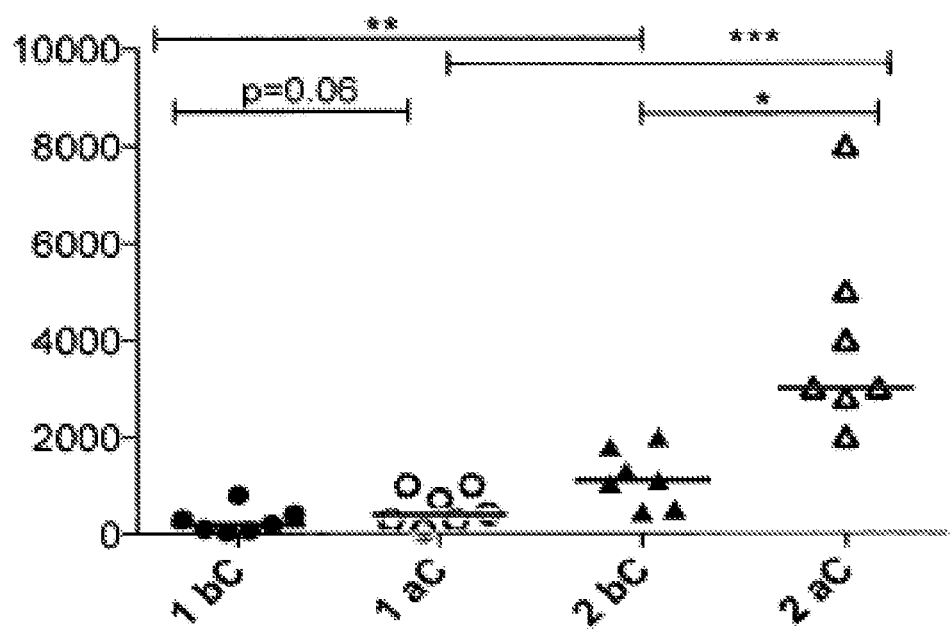

FIG. 10. Antibody titers in intraperitoneally vaccinated mice before and after a challenge with soluble HBsAg. Mice were vaccinated 3 times with a vaccine that did not comprise macro-aggregated IL-2 (group 1) or that did comprise macro-aggregated IL-2 (group 2). After completion of the vaccination course the mice were left untreated for 139 days. Then they were challenged with a single dose of soluble, not alum-adsorbed, HBsAg. Such challenge with free antigen after a long time of "rest" resembles an infection. Antibody titers were determined before and after the challenge with soluble HBsAg. The Y-axis shows the observed antibody titers, the X-axis presents the different groups. 1 bC: Group 1 before challenge; 1 aC: Group 1 after challenge; 2 bC: group 2 before Challenge; 2 aC: group 2 after challenge. Significant differences are shown with asterisks, the median value is represented with a line. Animals previously vaccinated with alum.-adsorbed IL-2 macro-aggregates as adjuvant show not only significantly enhanced antibody after the challenge but also show extremely significant enhanced antibody titres when compared to the titres seen in animals vaccinated with HBsAg without the IL-alum adjuvant.

Figure 11A:
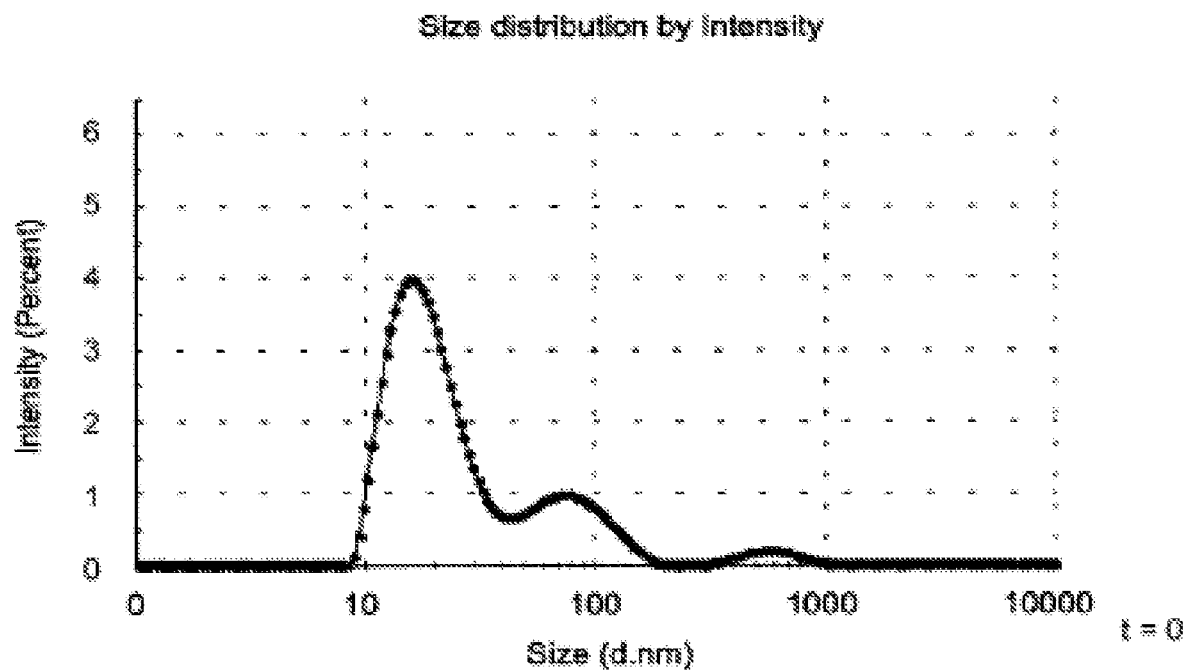

FIG. 11A. Time-dependent changes in the size distribution of IL2-agglomeration determined by measurement of intensity of scattering (t=0).

Figure 11B:
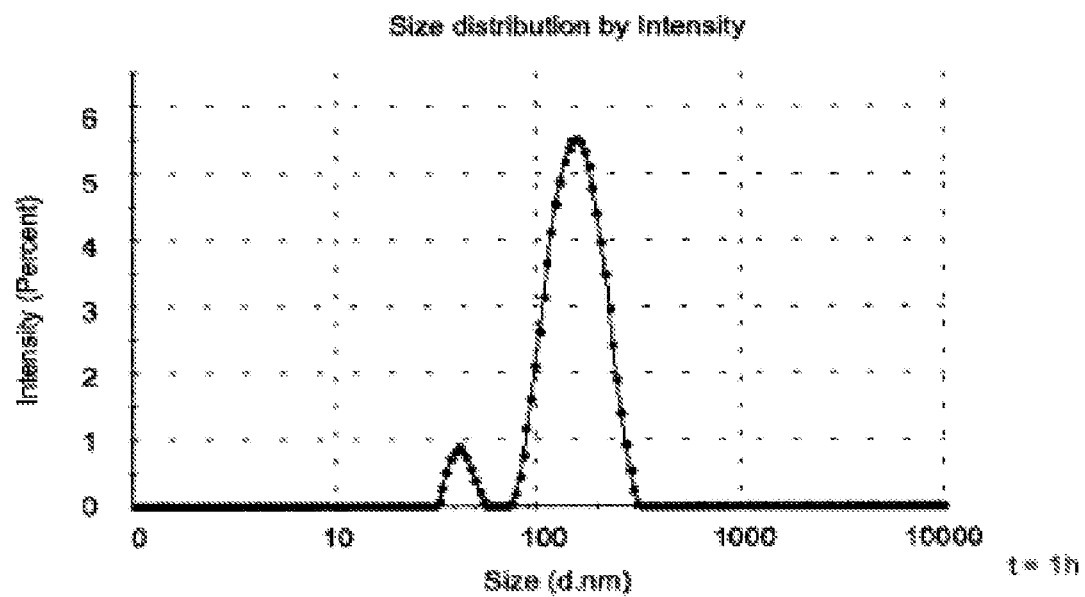

FIG. 11B. Time-dependent changes in the size distribution of IL2-agglomeration determined by measurement of intensity of scattery (t=1 h).

Figure 11C:
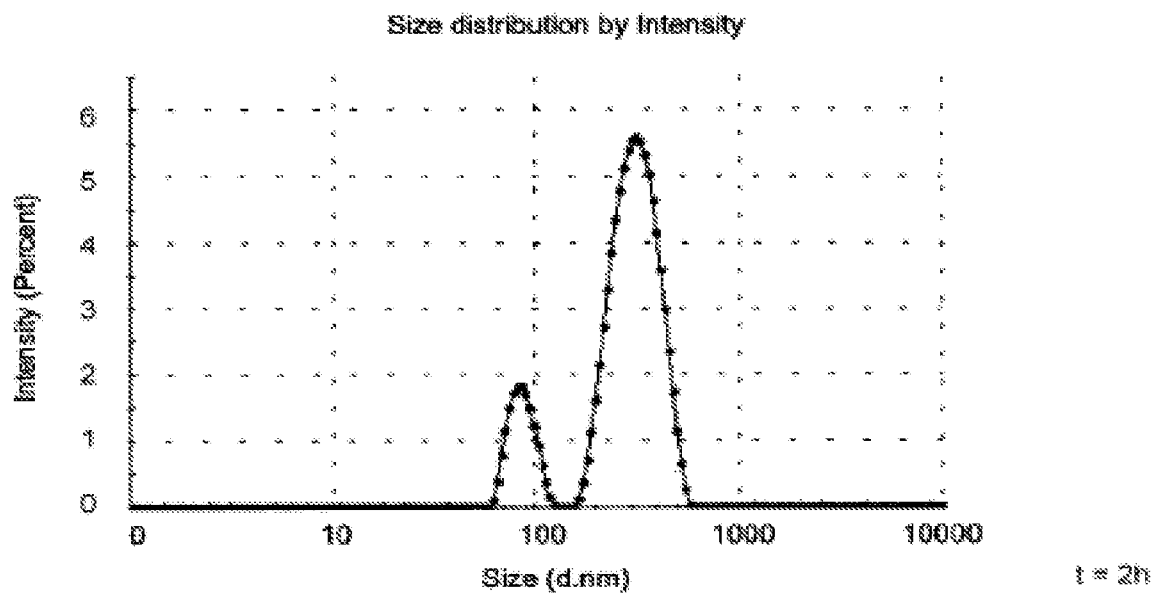

FIG. 11C. Time-dependent changes in the size distribution of IL2-agglomeration determined by measurement of intensity of scattery (t=2 h).

Figure 11D:
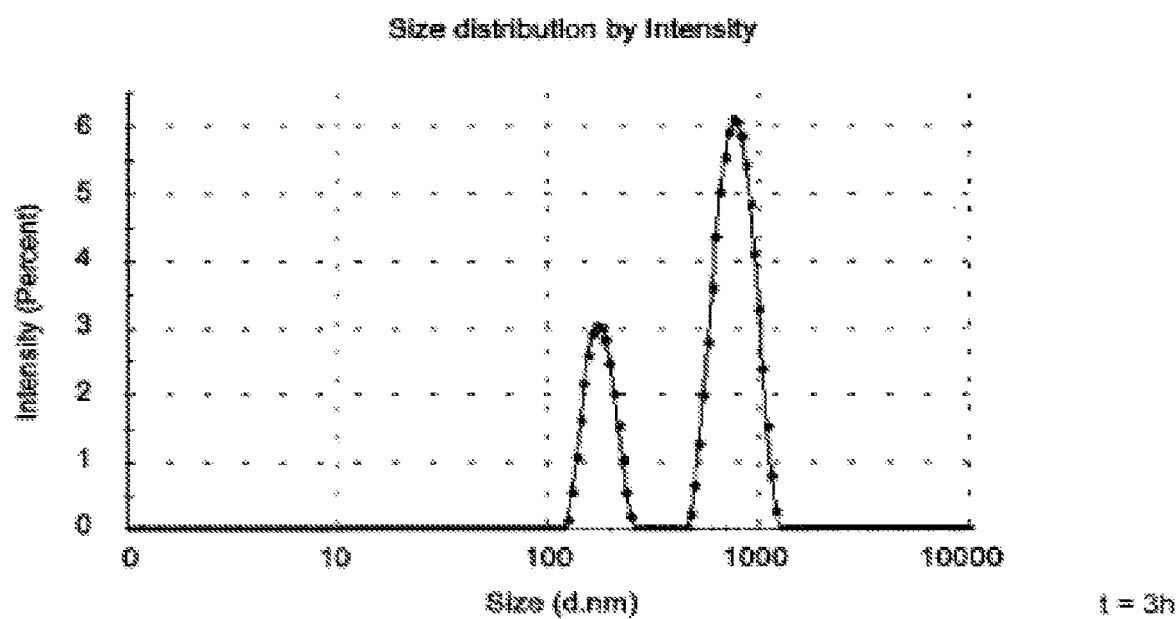

FIG. 11D. Time-dependent changes in the size distribution of IL2-agglomeration determined by measurement of intensity of scattery (t=3 h).

Figure 11E:
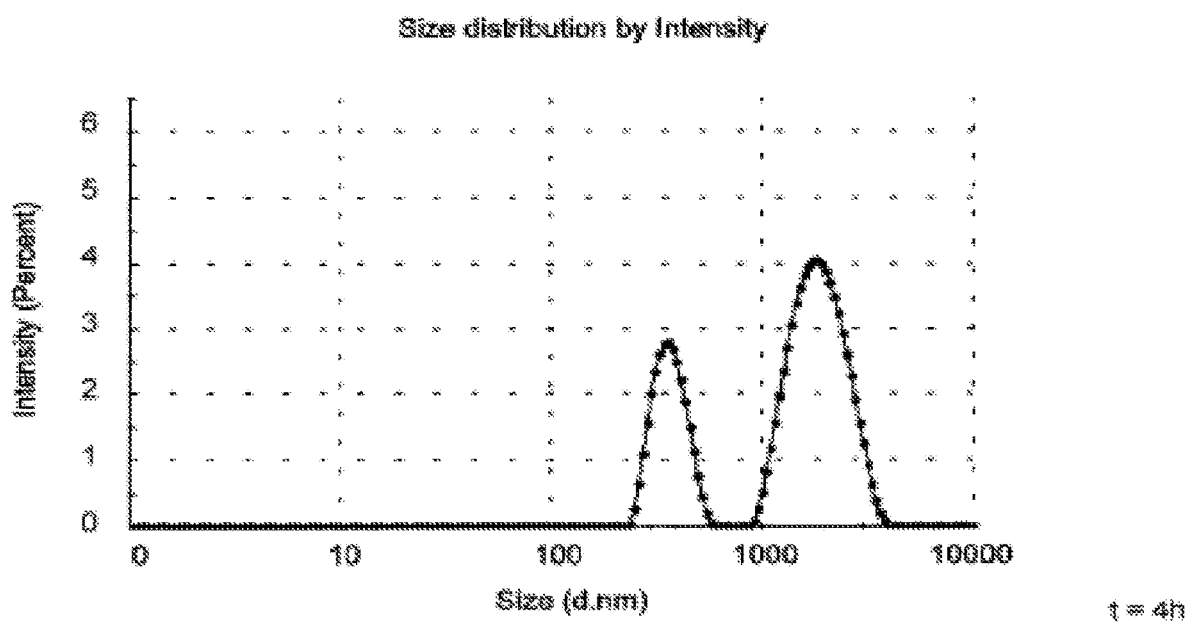

FIG. 11E. Time-dependent changes in the size distribution of IL2-agglomeration determined by measurement of intensity of scattery (t=4 h).

Figure 12:
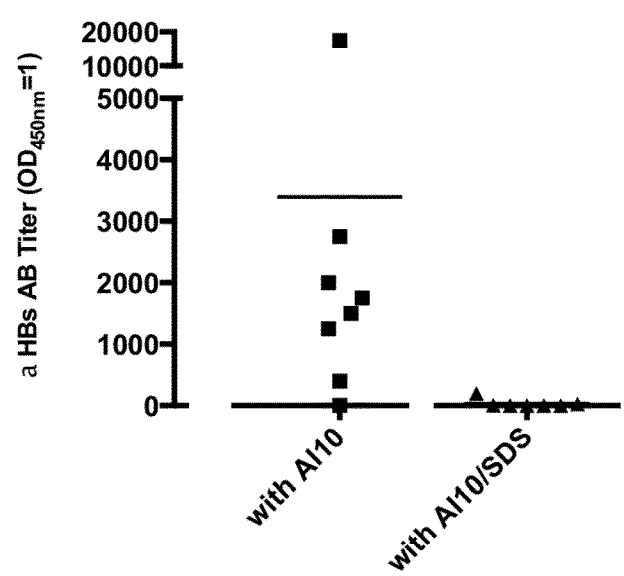

FIG. 12. Antibody titers 14 days after secondary injection in mice vaccinated with 1.0 μg of HBsAg adsorbed to 10 μg of alum mixed with 10 μg of rhuIL-2 adsorbed to 10 μg of alum in the absence (left) and the presence (right) of SDS.

DESCRIPTION OF THE INVENTION

A composition comprising cytokines, wherein a substantial amount of said cytokines are present in cytokine macro-aggregates, and wherein said cytokine macro-aggregates are associated with each other by:
    adsorption to a depot material, and/or
    encapsulation in liposomes.

The term "aggregates" refers to a combination of molecules, in particular cytokine molecules that are gathered together to form an individual body. In a preferred embodiment, aggregates contain molecules that non-covalently interact with each other.

The term "cytokine macro-aggregates" or "macro-aggregates" means aggregates of cytokine molecules that are larger than micro-aggregates, which contain typically from 2 to about 30 molecules, having diameter sizes from about 1 to about 10 nm. Macro-aggregates may be defined by their diameter. In a preferred embodiment, macro-aggregates are aggregates that have a diameter larger than 50 nm. In a further embodiment, macro-aggregates have a diameter larger than 75 nm, more in particular larger than 100 nm. Different techniques are known to the skilled person to measure diameter sizes of aggregates, such as dynamic light scattering or measurements from electron microscopy. Macro-aggregates may also be defined by the number of cytokine molecules contained therein. In a preferred embodiment, macro-aggregates are aggregates that contain at least 100 molecules. In a further embodiment, macro-aggregates are aggregates that contain at least 200, 300, 500, 750, or 1000 molecules. In another further embodiment, macro-aggregates are aggregates that contain at least $10^4$, $10^5$, or $10^6$ molecules.

In the context of the invention, "a substantial amount of said cytokines are present in cytokine macro-aggregates" means that a non-negligible part of the cytokines comprised by the composition is present in macro-aggregates. Thus, part of the cytokines may be present in the form of individual cytokine molecules and/or micro-aggregates with sizes below 20-50 nm. For example, part of the cytokines (e.g. IL-2) may be present in micro-aggregates of 9-17 nm, such as e.g. found in a typical Proleukin® solution. In a particular embodiment, at least 3% of the cytokines that are associated with each other in the composition are present in cytokine macro-aggregates. In another particular embodiment, at least 3% of the cytokines comprised by the composition are present in cytokine macro-aggregates. In another particular embodiment, at least 5, 7, 10, 15, 20, 25, 30, 35 or 40% of said cytokines are present in cytokine macro-aggregates. In a further embodiment, at least 50% of said cytokines are present in cytokine macro-aggregates. In another embodiment, the average diameter of the cytokine aggregates comprised by the composition is larger than 20 nm. In another particular embodiment, the average diameter of the cytokine aggregates associated with each other is larger than 20 nm. In yet another embodiment, said average diameter of cytokine aggregates is at least 25, 30, 40, 50, 60, 75, 100, 150 or 200 nm.

It is well known that most of Bio-Pharmaceuticals produced by recombinant technology suffer from a tendency to form aggregates (Wang W. Instability, stabilization, and formulation of liquid protein pharmaceuticals. Int J Pharm. 1999; 185:129-188).

There are several reasons for that:
1. most of these pharmaceutically active proteins are small and show a high degree of hydrophobicity
2. due to the lack of glycosylation, hydrophobicity is further increased when the protein is produced by recombinant technology in *E. coli*.

Aggregation also depends on pH (more aggregates at higher pH), concentration, temperature and the salinity of the cytokine solution. In the past, it was commonly accepted that the aggregation of the active principles within these Bio-Pharmaceuticals should be avoided.

Hence, when used, these Bio-Pharmaceuticals are dissolved in buffers comprising aggregation-preventing agents like sodium dodecyl sulfate, to prevent molecule-to-molecule aggregation with the formation of large aggregates. Such as for example described in EP 1 688 146 A1, where a minimal amount of SDS as an aggregation-preventing agent is required to obtain IL-2 micro-aggregates with the desired therapeutic characteristics.

It has now surprisingly been found, that compositions comprising depot-attached cytokines in such large macro-aggregate states are more effective than when in micro-aggregated state in generating an active specific immunotherapy for cancers.

Within a typical embodiment of the subject application, the cytokines are present as aggregates of various molecular masses. Such aggregates may be obtained in the absence of aggregation-preventing agents, or in the presence of an aggregation-preventing agent in an amount sufficiently low to allow formation of cytokine macro-aggregates. It will be appreciated by the skilled person that the cytokine macro-aggregates in a composition of the invention can be formed in several ways. Cytokine aggregates may be formed before mixing the cytokines (macro-aggregates) with the other components of the composition, or (non-aggregated or micro-aggregated) cytokines may be mixed directly with other components under conditions that allow or stimulate cytokine macro-aggregate formation.

In a particular embodiment, the composition of the invention comprises one type of cytokine, selected from the group consisting of IL-2, IL-4, IL-12, GM-CSF, and IFN-alpha. In a preferred further embodiment, the composition of the invention comprises IL-2 macro-aggregates.

In another particular embodiment, the composition of the invention comprises different cytokines in macro-aggregated form. Particularly cytokines independently selected from the group consisting of IL-2, IL-4, IL-12, GM-CSF, and IFN-alpha. In a preferred further embodiment, at least one cytokine is IL-2. In another preferred embodiment, the composition of the invention comprises IL-2 and one or more cytokines selected from the group consisting of IL-4, IL-12, GM-CSF, and IFN-alpha; in particular IL-4 or GM-CSF; more in particular GM-CSF. Such a composition comprising macro-aggregates of different cytokines can be obtained in several ways. As an example, macro-aggregates of a first cytokine may be prepared and macro-aggregates of a second cytokine may be prepared and these may be mixed before associating them with each other by adsorbing them to a depot material and/or encapsulating them in liposomes. Another exemplary option is to generate macro-aggregates directly from a solution containing several types of cytokines, thereby generating macro-aggregates that contain different cytokines and using these macro-aggregates to associate them with each other. A third example is to prepare macro-aggregates of a first cytokine and associate these with each other; prepare macro-aggregates of a second cytokine and associate these with each other; and subsequently mix the associated macro-aggregates. When using adsorption to a depot as a means to associate macro-aggregates, this last option allows generating depot materials with the highest possible density of a particular cytokine. E.g. one alum particle may be covered by IL-2 macro-aggregates, while a second alum particle may be covered by IL-4 macro-aggregates.

As it is one of the objectives of the present invention to provide that the present compositions and their components, in particular as vaccine formulation, will participate both in the local processes at the site of the inoculation site, and in the lymph nodes where the actual specific immune process is induced, it is desirable to combine different cytokines in macro-aggregated form in the composition. Using different cytokines it becomes possible to stimulate several arms of the immune system, e.g. IL-2 stimulates T cells and enhances the activity of NK cells; GM-CSF & IL-4 are involved in recruitment and maturation of dendritic cells; GM-CSF in addition induces vascularization of the inoculum; IL-12 activates dendritic and other immune cells; and IFN-alpha recruits and activates NK cells.

Thus in a particular embodiment of the present invention one or a plurality of different cytokines are present as macro-aggregates within the composition; and in particular each cytokine being independently selected from the group consisting of IL-2, IL-4, IL-12, GM-CSF and IFN-alpha.

As will be apparent to the skilled artisan, the aforementioned cytokines are only provided as possible examples and have no intention to restrict the cytokines macro-aggregates used in the compositions of the present invention. Said cytokines have been selected on the basis of currently available knowledge about cytokine action, but also on the basis of physical availability of these cytokines in pharmaceutical quality. In the future other cytokines may become available and added to the compositions of the present invention according to their described activity.

In principle such a combination of different cytokine macro-aggregates adsorbed to the depot can be achieved by admixing the cytokines/cytokine macro-aggregates prior to associating them with each other, but in a preferred embodiment the different cytokines/cytokine macro-aggregates are separately adsorbed to the depot material and mixed afterwards.

As described above, in the composition of the present invention, cytokine macro-aggregates are associated with each other by adsorption to a depot material and/or encapsulation in liposomes. Thus, in a particular embodiment, the composition of the present invention comprises cytokine macro-aggregates that are associated with each other by adsorption to a depot material. In another particular embodiment, the cytokine macro-aggregates are associated with each other by encapsulation in liposomes. In a further embodiment, part of the cytokine macro-aggregates are associated with each other by adsorption to a depot material and part of the cytokine macro-aggregates are associated with each other by encapsulation in liposomes, and the adsorbed and the liposome-encapsulated cytokine macro-aggregates are then mixed.

In the compositions of the present invention the depot-attached cytokine macro-aggregates are either non-covalently bound to the depot material or covalently attached thereto using art known procedures. The term "adsorbed" as used within the subject application thus encompasses any kind of adsorption, i.e. the adsorption may be a physisorption or chemisorption caused by electrostatic attraction, van der Waals forces and/or covalent bonding.

In any case, when covalently bound to the depot material, the covalent binding should be reversible such that the cytokines can be released from the depot material. The skilled person is well aware on how to covalently and reversibly bind cytokine macro-aggregates to a depot material. For example, linkages may be used that can be degraded by (naturally occurring) enzymes or by chemical degradation. For example, a disulfide-bridge can be used as linker, that is cleaved by means of reductases in the living organism; or ester linkages can be present which can be degraded by esterases.

In principle any depot material typically used in the manufacture of vaccine compositions and capable of binding the cytokine macro-aggregates can be used. In one embodiment, and given the fact that the cytokine macro-aggregates are capable of binding to irradiated cells directly, the depot material consists of the irradiated tumor cells. Consequently, and in a particular embodiment of the present invention the depot material is selected from the group consisting of aluminum hydroxide, calcium phosphate, latex beads, polylactic acid-based microspheres or nanoparticles, and irradiated tumor cells (including irradiated autologous tumor cells, irradiated allogeneic tumor cells, and irradiated xenogeneic tumor cells). In another particular embodiment the depot material is selected from the group consisting of aluminium hydroxide, calcium phosphate, latex beads, and polylactic acid-based microspheres or nanoparticles; in particular the depot material is aluminium hydroxide. In another particular embodiment the depot material are latex beads or medicinal coal.

As described herein before, in another embodiment the compositions according to the present invention are further characterized in that the cytokines and/or the cytokine aggregates are associated with each other by encapsulation in liposomes. In a preferred embodiment DMPC liposomes (dimyristoylphosphatidylcholine) are used, but other components (e.g. phospholipids) for the preparation of liposomes can be used as well.

Any art known procedure to prepare (e.g. DMPC) liposomes can be used; for example a simple procedure is possible in which the cytokines are not treated under stress condition. In said procedure crystallized/lyophilized DMPC is just added to a concentrated cytokine solution containing a substantial amount of cytokine macro-aggregates and mixed, frozen and thawed in several cycles. The result are small liposomes that have encapsulated the cytokine macro-aggregates.

The exemplary procedure:

300 mg lyophilized DMPC (sterilized by irradiation) are added to a suspension of 1.0 mg cytokine/cytokine macro-aggregates in 1.0 ml buffer.

The mixture is vortexed for 1 min. and sonicated in a ultrasonic bath for 1 min.

Then the suspension is frozen for 5 min in a bath of dry ice in ethanol and thawed in a water bath at 37° C.

This procedure is repeated 3 times.

In the suspension obtained most of the cytokine macro-aggregates in the starting material are encapsulated in the generated liposomes, part of it is still free in the suspension.

Aliquots of the whole suspension thus obtained, and containing the desired amount of cytokine macro-aggregates are applied in composition of the invention.

In a preferred embodiment, the composition of the invention further comprises antigenic material. It is accordingly also within the present invention to provide the use of depot-attached cytokine macro-aggregates, optionally still including free cytokine molecules or cytokine micro-aggregates, in a composition with antigenic material. In a particular embodiment, said antigenic material is a microbial or tumor-associated antigenic material. In a more particular embodiment, said antigenic material is microbial-associated antigenic material. Microbial antigens are antigens of a microorganism and include, but are not limited to, viral, bacterial, parasitic and fungal antigens. Microbial antigens may be intact microorganisms, and natural isolates, fragments, or derivatives thereof, synthetic compounds which are identical to or similar to naturally-occurring microbial antigens and, preferably, induce an immune response specific for the corresponding microorganism (from which the naturally-occurring microbial antigen originated). In one embodiment, the antigen is a viral antigen. In another embodiment, the antigen is a bacterial antigen. In another particular embodiment, the antigen is a parasitic antigen. In yet another embodiment, the antigen is a pathogenic antigen. In another particular embodiments, the pathogenic antigen is a synthetic or recombinant antigen.

In another particular embodiment, the antigenic material is tumor antigenic material, such as material selected from the group consisting of irradiated autologous tumor cells, irradiated allogeneic tumor cells, irradiated xenogeneic tumor cells, tumor cell homogenates, tumor cell extracts, individual tumor antigens (natural or recombinant), mixtures of tumor antigens (natural or recombinant), peptides of tumor antigens (natural or recombinant). In a preferred embodiment, soluble antigens, especially non-particulate antigens, are rendered particulate by attaching them to a depot material.

In any case, in the manufacture of a composition according to the present invention, wherein the cytokines macro-aggregates are adsorbed to a depot material, the cytokine macro-aggregates are applied to the depot material in the highest possible density (μg of cytokine per μg of depot material). Under said circumstances the cytokine is released from the depot with release levels that are in the same range as those observed in clinical trials with cytokine gene transfected (tumor) cells. However, in contrast to the static release of cytokines observed in the clinical trials with cytokine gene transfected cells, the release of cytokines from the cytokine macro-aggregates associated by adsorption to a depot is dynamic, with a high release burst within the first hours and a low level long term release (see FIG. 7A). As is evident from FIG. 7B, underloading of the depot has a negative effect on the release levels and release pattern and survival (see Kaplan Meyer survival plot—FIG. 8).

In a particular embodiment of the compositions as described herein, the depot is aluminium hydroxide (alum) and the weight ratio of alum to cytokine (also called density) is between 1:10 and 30:1; more in particular between 1:1 and 3:1; even more in particular 1:1.

A preferred composition according to the present invention, is said wherein 1-30 μg of recombinant IL-2 (Proleukin), 1-30 μg of recombinant GM-CSF, 1-30 μg of recombinant IL-4, 1-30 µg of recombinant IL-12, or 1-30 µg of recombinant IFNalpha is adsorbed in a ratio between 10:1 and 1:10 of cytokine to alum.

A more particular composition of the present invention is said composition, wherein 10 µg of recombinant IL-2 (Proleukin), 10 µg of recombinant GM-CSF, 10 µg of recombinant IL-4, 3 µg of recombinant IL-12, or 10 µg of recombinant IFNalpha is each adsorbed in a ratio of 1:1 of cytokine to aluminum hydroxide.

As will be apparent from the experimental part hereinafter, the compositions of the present invention are particularly useful for the stimulation of immune responses, such as for example in the generation of host immunity against cancer (e.g., a tumor) or a pathogen (e.g. infectious bacteria or viruses or subunits (antigens) of them). It is accordingly an embodiment of the present invention to provide a composition as described herein before for use as a medicament; in particular for use as a human or veterinary medicine. In another embodiment, the present invention provides compositions for use as a vaccine. In a particular embodiment, the present invention provides compositions for use as a microbial vaccine. In another particular embodiment, the present invention provides compositions for use as a cancer vaccine.

In yet another embodiment, the invention provides a composition for use in the treatment of a disease in a mammal, in particular for use in the treatment of an infectious disease or cancer. In a further embodiment, the present invention provides a composition for use in the treatment of cancer; in particular a cancer selected from the group consisting of renal, liver, lung, ovarian, prostate, pancreatic, stomach, head and neck, testicular carcinoma, fibrosarcoma, melanoma, glioblastoma, lymphomas, leukemias and myelomas. In a further embodiment, the invention provides a composition for use in the treatment and/or prevention of a cancer selected from the group consisting of renal carcinoma, pancreatic carcinoma, colon carcinoma, prostate carcinoma, and melanoma; in particular renal and pancreatic carcinoma and melanoma. In another embodiment, the invention provides a composition for use in the treatment and/or prevention of renal carcinoma and melanoma. In a particular embodiment, the present invention provides a method for the treatment and/or prevention of a disease, such as an infectious disease or cancer, said method comprising administering a composition of the invention to a subject in need thereof.

It particularly relates to the area of active specific immunotherapy of cancer ("cancer vaccines"), and provides the use of the compositions as described herein, in the preparation of therapeutic vaccines that can eliminate cancer cells. Compared to and different from art known cytokine depot formulations, the macro-aggregate cytokine depot formulations of the present invention extends the immune reaction beyond the local reactions at the inoculation site and even enhances the induction of tumor-specific immune reactions at the level of the lymph nodes.

In another particular embodiment, the present invention provides a composition for the treatment and/or prevention of an infectious disease, such as a disease caused by infectious (microbial) pathogens, including bacteria, viruses, parasites and fungi. In some embodiments, treatment as used herein with reference to infectious pathogens refers to a prophylactic treatment which increases the resistance of a subject to infection with a pathogen or decreases the likelihood that the subject will become infected with the pathogen; and/or treatment after the subject has become infected in order to fight the infection, e.g., reduce or eliminate the infection or prevent it from becoming worse. In a particular embodiment, the method is a prophylactic treatment.

Under the influence of the macro-aggregate cytokine depot formulations of the present invention, it has been found by the present inventors that dendritic precursor cells differentiate into mature dendritic cells in situ, i.e. at the inoculation site. This in itself is already a significant improvement when compared to the complicated in vitro dendritic cell maturation as currently applied in dendritic cell based vaccines, but in addition to the in situ maturation of dendritic precursor cells, the macro-aggregate cytokine depot formulations of the present invention also enhance the antigen-specific immune reactions at the level of the lymph nodes. To said extent the dendritic cells bind and/or take up, in addition to antigenic fragments, cytokine aggregates, either or not still adsorbed to alum particles, at the inoculation site and carry them to the lymph nodes draining said inoculation site. In the lymph nodes antigen fragments (e.g. from a tumor cell, a bacterium, or a virus) are presented to T-cells and NK cells at the lymph node, thus activating the former cells into antigen specific and cytotoxic T-cells and NK cells. The presence of cytokine-loaded particles in the lymph nodes interacts with these processes and further strengthens antigen presentation and cell stimulation.

The import of cytokine aggregates into the highly organized lymph node environment is a hitherto unknown possibility to manipulate the immune reactions on the level of the lymph nodes.

Further effects of the macro-aggregate cytokine depot formulations of the present invention can be seen at the site of the inoculum. Again compared to and different from art known depot formulations, the inoculum based on the depot formulations with depot-attached cytokine macro-aggregates of the present invention develops into a vascularized nodule, preserving the antigenic material (e.g. irradiated tumor cells) and the cytokine depot material. As such this vascularized nodule appears to the T-cells, that have been specifically activated in the lymph nodes, as an artificial tumor or infection site and enables re-stimulation of the activated T-cells by the remaining cytokines and original antigenic material. This process of renewed contact with the vaccine antigens further enhances the stimulation of immune responses by the cytokine depot formulations of the present invention.

In addition, it has been observed that the vaccine compositions of the present invention provide a faster and higher immunogenic response than comparable compositions that lack cytokine macro-aggregates. Therefore, the compositions of the present invention allow for a faster immunization and allow for the immunization of otherwise non-respondent subjects.

It is a further object to provide a process for preparing the composition of the invention, comprising the steps of:
a) providing an aqueous solution comprising a cytokine; wherein said aqueous solution contains no aggregation-preventing agent, or an aggregation-preventing agent in an amount sufficiently low to allow formation of cytokine macro-aggregates with a diameter larger than 50 nm;
b) incubating said aqueous solution for a time sufficient to aggregate a substantial amount of said cytokine into cytokine macro-aggregates with a diameter larger than 50 nm;
c) associating said cytokine macro-aggregates by
   mixing said aqueous solution with the depot material, to
      adsorb said cytokine aggregates to the depot material;
      and/or
   encapsulating said cytokine aggregates in the liposomes.

Given the importance to obtain cytokine macro-aggregates, it is preferred to provide an aqueous solution comprising a cytokine, wherein said solution does not contain aggregation-preventing agent, or an aggregation-preventing agent in an amount sufficiently low to allow formation of cytokine macro-aggregates. For example, Il-2 is often distributed in the presence of SDS as an aggregation-preventing agent, since it has been found that for prior art applications, when SDS is present in an amount larger than or equal to 95 µg SDS per mg cytokine, macro-aggregate formation is prevented (see e.g. EP1688146). When preparing the composition of the invention, such macro-aggregates are exactly required; therefore, when starting from such an SDS-containing solution, the solution can be diluted so that it contains less than 95 µg SDS per mg cytokine. In a particular embodiment, the dilution is performed in phosphate buffered saline (PBS).

The inventors have found that aggregate formation tends to be a time-dependent process, i.e. when formation of aggregates is allowed, aggregates tend to grow over time. Macro-aggregates may be made according to the procedures described herein. For example, by diluting an SDS-containing cytokine solution with PBS, so that the SDS concentration is lowered below 95 µg per mg cytokine, at which concentration macro-aggregates are formed relatively rapidly. However, macro-aggregates may be formed at even lower concentrations of SDS, or complete absence of aggregation-preventing agents, thereby reducing the time in which macro-aggregates are obtained. Vice-versa, aggregation-preventing agents may present in slightly higher amounts, which necessitates longer incubation times for macro-aggregate formation, but still allow macro-aggregate formation to obtain a composition of the invention.

When the composition of the invention comprises antigenic material, as described above, the above process may further comprise step
d) contacting said solution comprising associated cytokine macro-aggregates with antigenic material.

EXAMPLES

Example 1

Binding of IL-2 to Alum Using IL-2 Diluted in PBS

Recombinant human IL-2 (rhuIL-2, Proleukin/Roche) was used for this experiment. The lyophilized 1.1 mg recombinant protein was dissolved in 1.1 ml of pure water. 180 µg of SDS is present as an aggregation-preventing agent in the Proleukin product, thus, the solution contains appr. 164 µg per mg IL-2. At this concentration, IL-2 is predominantly present in micro-aggregates of appr. 9-17 nm.

The vaccine was prepared for vaccination of 8 animals, each receiving 0.2 ml with an excess of about 20%.
Materials:
Rehydragel HPA, fluid gel (Reheis Inc. Berkeley heights NJ) was used.
Concentration: 2.0%(=20 g/l) of aluminum oxide.
Preparation of the Vaccine Components:
1. 500 µl alum suspension, containing 100 µg of alum was prepared from the Rehydragel fluid gel stock by dilution with PBS buffer.
2. 500 µl of IL-2 macro-aggregate solution was prepared by diluting 100 µl of the rhuIL-2 solution with 400 µl PBS buffer. Thereby, the SDS concentration is lowered to about 33 µg per mg IL-2, allowing formation of macro-aggregates as further demonstrated in the size distribution experiment shown in FIGS. 11A-E.

Preparation of the Alum-adsorbed Cytokine Macro-Aggregates

In order to mix the two components very fast, both solutions were mixed by pipetting them simultaneously very fast into a tube, which was, at the same time, vigorously shaken on a vortexer. The mixture is further incubated for 1 h on a roller at room temperature.

The result is a suspension of alum-adsorbed IL-2 macro-aggregates at a concentration of 10 µg IL-2 adsorbed to 10 µg alum in 1.0 ml.

In FIG. 1a-d, the IL-2-loaded alum macro-aggregates are shown. IL-2 is identified by incubation with a monoclonal IgG antibody specific for human IL-2 followed by incubation with an AlexaFluor 488 labeled Goat anti mouse IgG (h&l) antibody.

Figure 1B:
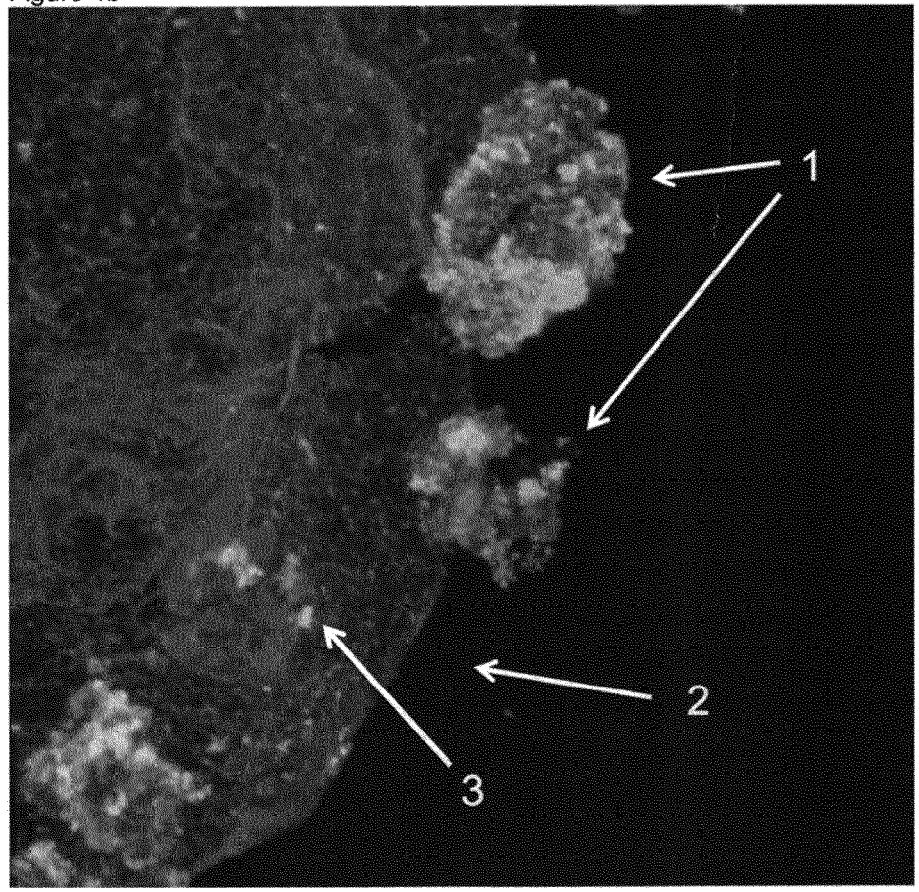

Macro-aggregates of IL-2 can be recognized in dot-like locations on a large lump of alum (FIGS. 1a and 1b). The large alum particle shown in FIG. 1 has a size of about 20×60 µm. The size of the dot-like IL-2 macro-aggregates on the alum matrix can be estimated to be between 50 nm and 6000 nm. IL-2 macro-aggregates of about 100 nm in size contain about $10^6$ IL-2 molecules, and these aggregates weigh about 10 femtograms. The largest IL-2 macro-aggregates in FIG. 1a are estimated to contain about $10^9$ IL-2 molecules, and weigh about 10 picograms. Since different cytokines are of similar molecular sizes, this calculation relates also to them.

Preparation of a Vaccine Comprising Tumor Antigenic Material

Irradiated RenCa murine renal carcinoma cells are labeled with Texas Red N-Hydroxy-Succinimide Ester.

The Texas Red-labeled irradiated tumor cells are suspended in PBS in a density of $10 \times 10^6$ cells per ml.

1.0 ml of the IL-2 macro-aggregates adsorbed to alum suspension and 1.0 ml of the cell suspension were mixed shortly before application.

Each mouse receives an injection of 200 µl containing:
$10^6$ irradiated tumor cells
10 µg of IL-2 adsorbed to
10 µg of alum When the tumor cells (stained with Texas Red) are added to the IL-2-alum macro-aggregates, they additionally aggregate with the IL-2-loaded alum lumps, as seen in FIG. 2. IL-2 is identified by incubation with a monoclonal IgG antibody specific for human IL-2, followed by incubation with an AlexaFluor 488 labeled Goat anti mouse IgG (h&l) antibody.

Macro-aggregates of IL-2 can be recognized in dot-like locations (2) on a large lump of alum. In FIG. 2 a typical alum particle is shown with attached cytokine aggregates in combination with antigenic material. The size of the alum particle ("lump") is about 20×80 µm. The complete "ready for injection" vaccine dose is composed of a million or more of such macro-aggregate coated alum particles of differing sizes (containing a total of 10 µg of IL-2 attached to 10 µg of alum and $10 \times 10^6$ tumor cells).

Tumor cells and tumor cell fragments (1) are identified by the red fluorescence of the Texas Red labeled tumor cells. Grey-scale conversion renders them grey.

Example 2

Binding of IL-2 to Alum Using IL-2 Diluted in the Original SDS-containing Buffer But for the buffer used, the procedure is exactly the same as described for Example 1 above. Instead of PBS a buffer is used that contains all the ingredients, among them SDS, as they are contained in the original lyophylisate in which rhuIL-2 (Proleukin) is provided by Novartis.

The further steps in the manufacture of the alum-adsorbed IL-2 and the complete vaccine containing irradiated RenCa tumor cells were the same as described in the procedure for Example 1.

In contrast to the immune fluorescence staining pattern obtained according to the procedure described in Example 1 the pattern obtained using the SDS containing buffer is completely different: Alum-attached rhuIL-2 is evenly/homogenously distributed over the alum particles, showing only slight aggregations in some localization (see FIG. 4a). As described in the Proleukin prescription information IL-2 treated by this procedure (180 μg SDS per mg of IL-2) is present in the form of soluble micro-aggregates of approximately 27 IL-2 molecules per aggregates. Such small micro-aggregates, corresponding to a molecular mass of approx. 500 kDa, can not be identified as isolated aggregates, such as shown in FIG. 2, but show the present homogeneous staining distribution instead.

The same composition was obtained when an IL-2 adsorbed to a depot material was made by following the instructions in US2002176845 (see FIG. 4b). FIG. 4b shows that compositions generated using the procedures of US2002176845 do not contain aggregates with a diameter greater than 50 nm.

Example 3

Comparison of Prior Art Formulations and a Composition of the Invention

The two types of vaccines were applied in therapeutic survival experiments.

In these therapeutic experiments the animals were treated with a lethal dose of $10^5$ vital RenCa tumor cells.

4 days later the animals were vaccinated with vaccines containing $10^6$ irradiated RenCa tumor cells and 10 μg IL-2 adsorbed to 10 μg alum
either in PBS (Example 1)
or in a SDS-containing buffer (Example 2).

When treated with vaccines that contained the IL-2 in macro-aggregate form adsorbed to alum (Example 1) more animals survived than in the group in which the animals were treated with vaccines containing IL-2 in monomeric or micro-aggregated form (Example 2).

Similar observations were made in experiments in which other cytokines were used.

Example 4

Use of Irradiated Tumor Cells as a Depot Material

In these experiments $10 \times 10^6$ B16 murine melanoma cells were incubated with 100 μg of rhuIL-2 (Proleukin) in macro-aggregated form, produced by dilution in PBS.

After incubation, the cells were centrifuged, and the supernatant was tested for the presence of unbound IL-2 by ELISA and by a biological test applying CTLL-2 cells as IL-2 indicators.
86% of the added IL-2 was bound to the tumor cells.
In a series of experiments, other irradiated tumor cells:
RenCa murine renal carcinoma,
C26 murine colon carcinoma,
Dunning rat prostate carcinoma,
FA 144 human renal carcinoma cells isolated from a patient's renal carcinoma,
FA 152 human renal carcinoma cells isolated from a patient's renal carcinoma.
were also "loaded" with IL-2 macro-aggregates.
The average loading rate was 85%.

This indicates that irradiated tumor cells unspecifically bind macro-aggregated IL-2, and can be used as a depot material in the formulations of the present invention.

After loading, the macro-aggregated IL-2 loaded cells were washed and the cell-bound IL-2 was identified using an IL-2 specific IgG antibody, followed by incubation with a Fluorescein-labeled goat anti mouse IgG antibody.

An example of macro-aggregated IL-2 loaded B16 murine melanoma cell is shown in FIG. 3. As can be clearly seen, staining is not homogeneous but spotty, indicating that IL-2 macro-aggregates have bound to the cell surface, when SDS-free PBS is used for macro-aggregate formation and loading.

Assuming a cell diameter of 10 μm the size of the adsorbed IL-2 aggregates can be estimated as being in the 50-100 nm range.

Such macro-aggregated IL-2-loaded cells have been used in therapeutic vaccination experiments, in which the mice were vaccinated with $10^6$ irradiated macro-aggregated IL-2-loaded RenCa renal carcinoma cells.

In these experiments the highest survival rate was obtained when the mice were vaccinated with $10^6$ irradiated tumor cells loaded with 30 μg of IL-2, from which a substantial amount is present in macro-aggregated form.

Similar observations were obtained with the other tumor cells indicated above. Consequently, in a particular embodiment according to the present invention, the depot material, present within the compositions as described herein, consists of irradiated cells, in particular irradiated tumor cells.

Example 5

Applying Different Cytokines in Macro-aggregated Form

In order to stimulate several arms of the immune system, a combination of cytokines can be applied.
IL-2 stimulates T cells and enhances the activity of NK cells
GM-CSF & IL-4 are involved in recruitment and maturation of dendritic cells
GM-CSF induces vascularization of the inoculum
IL-12 activates dendritic cells
IFNalpha recruits and activates NK cells.

By using such a mixture of cytokines several pathways, i.e. CD8 T-cells, NK cells, NKT cells, and antibodies, are activated that are important for the induction of an efficient anti-tumor immune response.

In an effort to evaluate the benefits of a combination of different cytokines in the depot formulations of the present invention, a vaccination experiments has been performed where mice were vaccinated against RenCa cells with either;
macro-aggregated GM-CSF adsorbed to alum;
macro-aggregated IL-2 adsorbed to alum;
macro-aggregated IL-4 adsorbed to alum;
macro-aggregated interferon alpha (IFNalpha) adsorbed to alum;
the combination of macro-aggregated IL-4 and macro-aggregated GM-CSF adsorbed to alum;
the combination of macro-aggregated IL-4, macro-aggregated GM-CSF, macro-aggregated IL-2 and macro-aggregated IFNalpha adsorbed to alum.

In preparing these multi-cytokine-vaccines one may either load each cytokine separately onto the depot (alum)

and subsequently mix the cytokine-alum adsorbates, or one may mix the cytokines and adsorb them as a mixture to the depot (alum).

For each of the cytokines the optimal dose of alum-attached cytokine was determined, and when used in combination with alum as the depot, the following cytokine dosages were determined:

For IL-2: 10 µg per vaccine dose
For IL-4: 3-10 µg per vaccine dose
For GM-CSF: 3-10 µg per vaccine dose
For IL-12: 1-3 µg per vaccine dose
For IFN alpha: 10-30 µg per vaccine dose.

The cytokine to alum binding ratio, should be such that the alum is saturated with the cytokine, most of which are in macro-aggregate form; in particular in a ratio of between and about 3:1 and 1:1; more in particular in a ratio of about 1:1.

For a first vaccination experiment the following preparations were used:
3 µg of IL-4 macro-aggregates were adsorbed to 3 µg Alum;
3 µg of GM-CSF macro-aggregates were adsorbed to 3 µg Alum;
and a mixture thereof.

After incubation and rolling, the cytokine-alum adsorbates were mixed and added to irradiated tumor cells.

About 43 µg of macro-aggregated cytokine-loaded alum and $10^6$ irradiated tumor cells were contained in each vaccine dose.

A total of 43 µg of alum per vaccine dose is still very low compared to the alum dose contained in conventional vaccines.

The vaccine was used for therapeutic tumor vaccination experiments.

For a second vaccination experiment the following preparations were used:

A control preparation containing a Texas Red Labeled antigen, an alum depot but lacking alum adsorbed cytokine macro-aggregates; and a macro-aggregated cytokine preparation containing a Texas Red Labeled antigen, and alum adsorbed macro-aggregated cytokines consisting of;

10 µg of macro-aggregated IL-2 were adsorbed to 10 µg Alum;
2 µg of macro-aggregated IL-4 were adsorbed to 2 µg Alum;
3 µg of macro-aggregated Interferon alpha were adsorbed to 3 µg Alum; and
3 µg of macro-aggregated GM-CSF were adsorbed to 3 µg Alum.

Mice were injected with said depot formulations and at various days microphotographs of tissue slices prepared from the inoculation sited of the mice were obtained. (See FIGS. 6a-d).

Figure 6A:
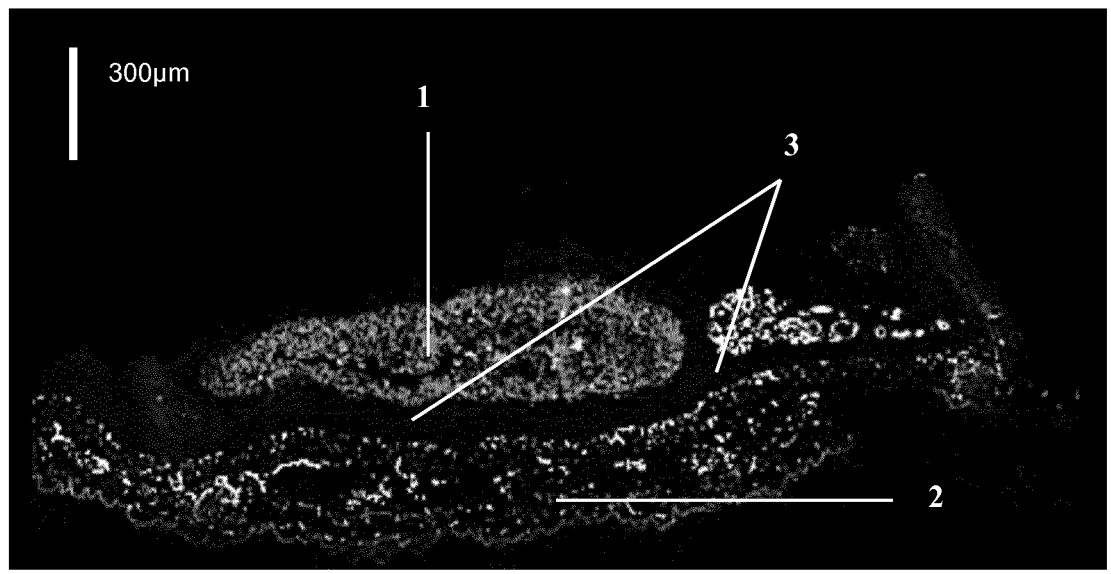
Figure 6B:
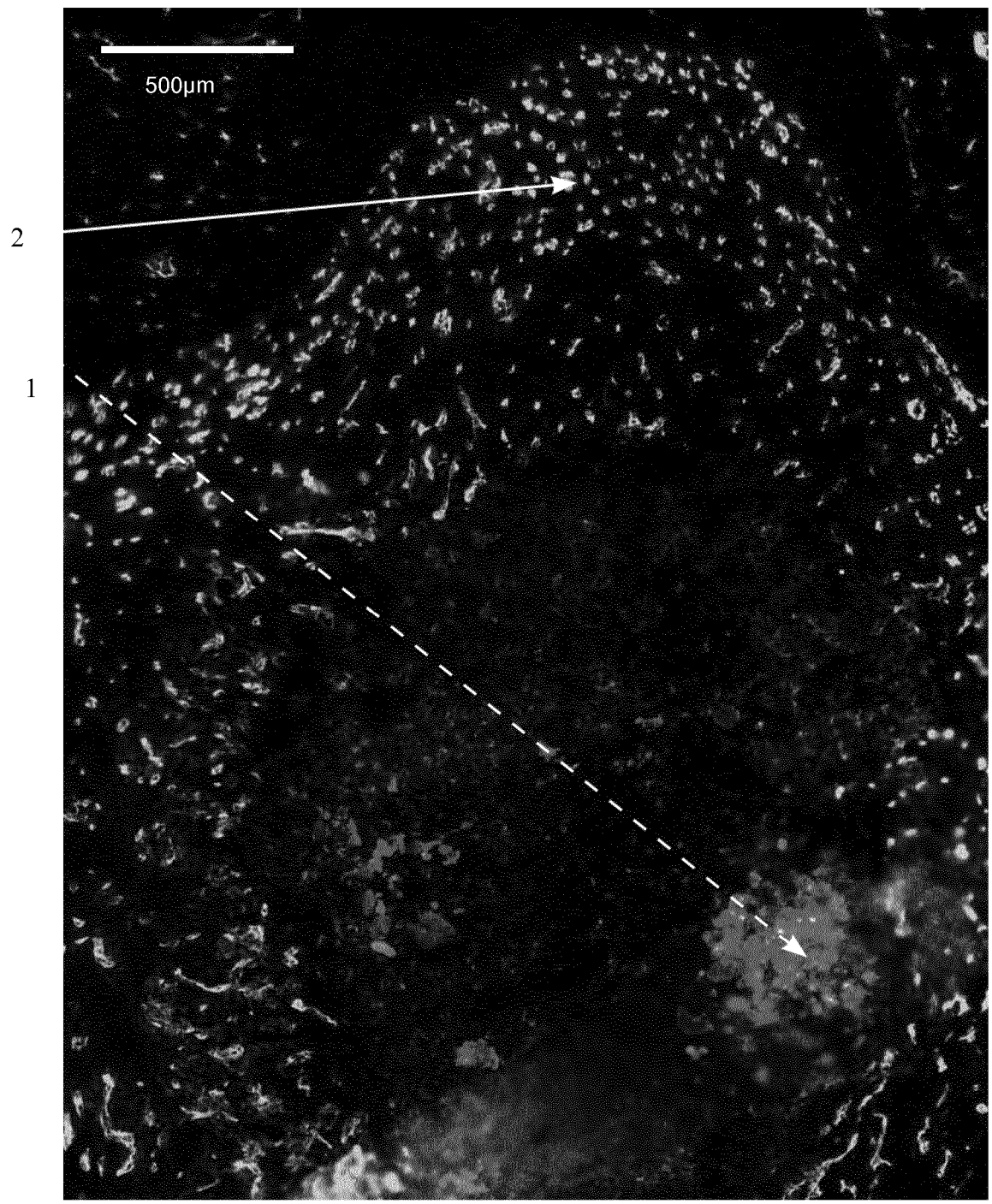
Figure 6C:
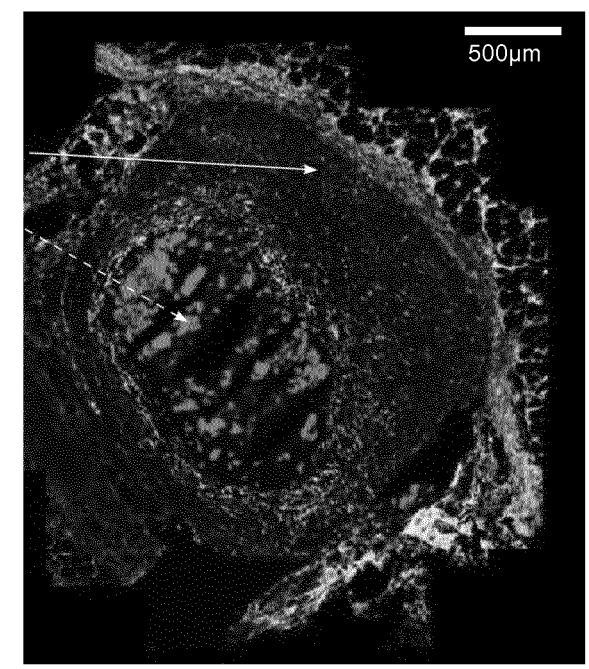

Neither capsule formation, nor any sprouting of capillaries in and around the inoculum are seen 11 Days after vaccination, in the tissue slices of the control preparation (FIG. 6a). In the tissue slices for the macro-aggregated cytokine preparation to the contrary, at 11 day after vaccination there is clear capsule formation and sprouting of capillaries in and around the inoculum (FIG. 6b).

Figure 6D:
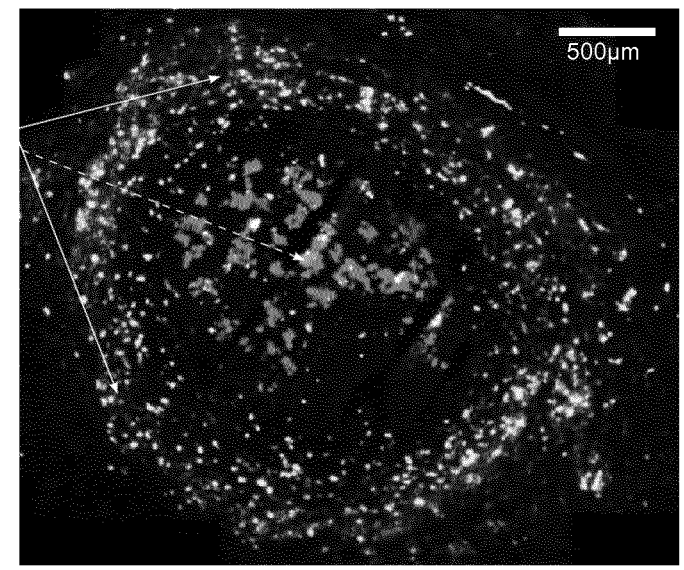

After 19 days, the inoculum of the macro-aggregated cytokine preparations is fully encapsulated (FIG. 6c) and vascularization of this capsule and inoculation site (FIG. 6b) allows CD4 helper T cells invading the capsule and the inoculum (FIG. 6d).

Figure 6E:
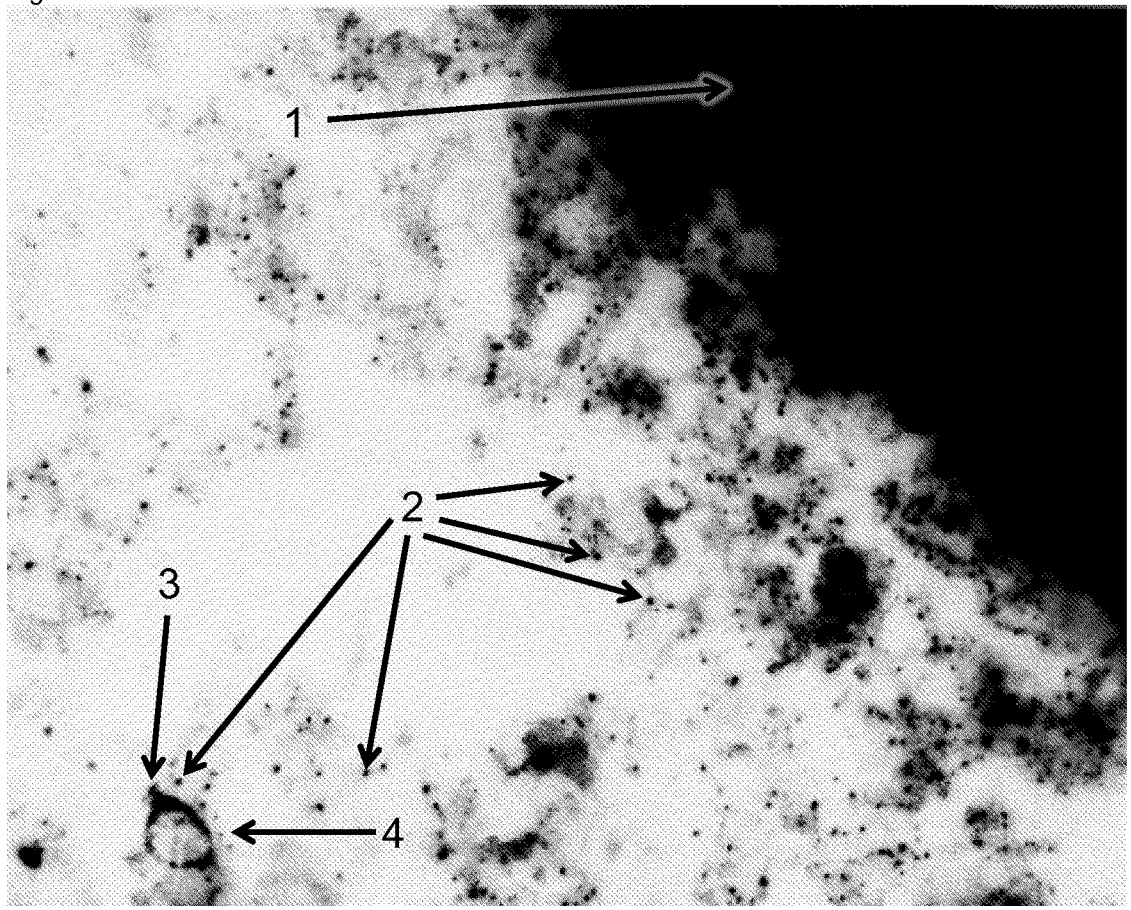
Figure 6F:
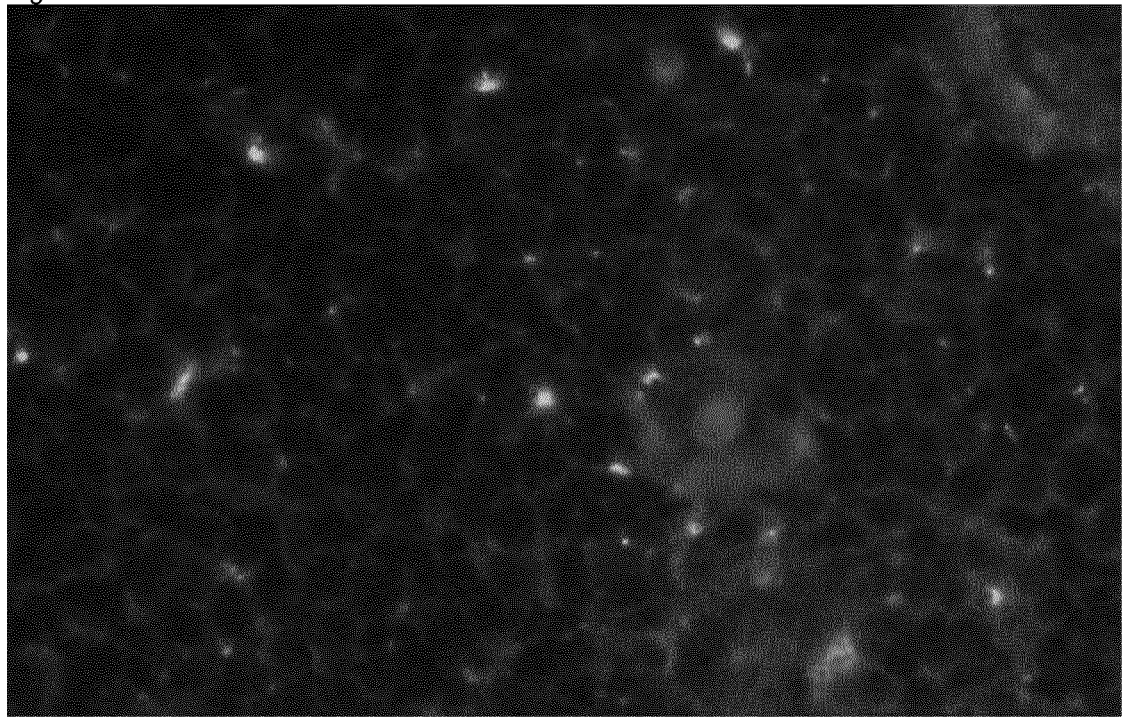

For a third vaccination experiment the following preparation was used:

A vaccine containing a Texas Red Labeled irradiated tumor cells, and alum adsorbed macro-aggregated IL-2. 24 hours after injection, tissue slices from the inoculum site and the draining lymph node were prepared and stained (FIGS. 6e and 6f, respectively). The area surrounding the inoculum side is swarmed with IL-2 macro-aggregates. A dendritic cell is seen taking up tumor antigenic material as well as binding IL-2 macro-aggregates. These dendritic cells transport the cytokine macro-aggregates to the lymph node that drains the inoculum area. This is evidenced by the presence of small IL-2 aggregates in said lymph nodes (FIG. 6f). Of interest is that, in the presence of IL-2, CD86+ dendritic cells expose CD25, which increases the affinity of the IL-2 receptor for its ligand (Boyment & Sprent, Nature Reviews Immunology 12: 180-190). It our likely these increased affinity receptors that bind the IL-2 macro-aggregates, thereby allowing their transport to the lymph node.

The abundance of IL-2 aggregates surrounding the inoculum site and how they appear in photographs may be explained as follows: large cytokine macro-aggregates associated with each other are injected. In the environment of the inflammatory fluid surrounding the inoculum, the cytokine macro-aggregates are not fully stable anymore and "explode" and release macro-aggregates of smaller size. These swarm the environment of the inoculum with smaller cytokine aggregates (i.e. micro- as well as macro-aggregates) and monomeric cytokines.

The results obtained clearly showed that the mixture of alum-adsorbed cytokines induced better immune responses than individual alum-adsorbed macro-aggregated cytokines and a higher percentage of animals survived (FIG. 5).

Moreover, applying mixtures of alum-adsorbed macro-aggregated cytokines in the vaccines yielded even better results than alum-adsorbed macro-aggregates of a single cytokine. As is evident from the foregoing, when used in combination the inoculum of the cytokine preparations develops properties of an artificial immune organ, comparable to a vascularized granuloma.

This artificial nodule-like organ has several very specific properties:
1. It keeps the inoculated tumor cells and the alum adsorbed cytokines for a long time in place;
2. It induces fibroblasts to form a capsule around it;
3. It induces sprouting of capillaries into the capsule and the inoculum, and, by this, provides long time "survival" and "nourishment" and prevents degradation and elimination of the inoculum;
4. Dendritic cells interact with the antigenic tumor cell material and the cytokine macro-aggregates and transport these to the lymph node; and
5. T-lymphocytes (and NK-cells) that have been specifically activated in the lymph node by dendritic cell-presented tumor antigens, patrol the organism and search for their target, tumor cells. The capillaries enable them to get into the inoculum and finally find their "real" target: tumor cells.

Consequently, in some respect, the inoculum imitates a tumor. Having the alum-loaded macro-aggregated cytokines in close proximity to the irradiated tumor cells in the inoculum, the former re-stimulate said circulating T cells (and other cells) when they meet their target at the inoculation site.

Taken together, the special properties of these macro-aggregated cytokine depot preparations allow manipulation of the immune response on the level of the inoculum and on the level of the lymph node. This procedure opens a way to manipulate the immune reactions in the lymph node by transport of multi-molecular deposits of biologically active cytokines into the lymph node.

Example 6

Preparation of Diphtheria Vaccine

IL-2 macro-aggregates adsorbed on alum were prepared according to example 1.

Diphtheria toxoid was adsorbed to alum as a depot material. 1 μg of toxoid adsorbed on 1 μg of alum was present per vaccination dose. This was mixed with different amounts of IL-2 macro-aggregate/alum complexes (0, 1, 3 or 10 μg per dose) to evaluate the addition of the depot-adsorbed cytokine macro-aggregates to viral vaccines.

Mice were injected 3 times with the vaccines and 14 days after the last application, sera were collected from the retro-orbital plexus. Antibody titers in sera were tested using ELISA with solid phase-adsorbed tetanus toxoid. Antibody titers were defined as the dilution at which the optical density at 450 nm reached 1.0 in the indirect ELISA.

| Dose of macro-aggregated IL-2 | Antibody titer |
|---|---|
| 0 | 1 |
| 1 | 20 |
| 3 | 300 |
| 10 | 10000 |

As can be seen from the results, the addition of depot-adsorbed cytokine macro-aggregates greatly enhances antibody titers in a dose-dependent relationship. Addition of 10 μg IL-2-alum increases Diphtheria antibody titers approximately 10000-fold. Thus, even when using very low amounts of antigenic material, the compositions of the invention allow for the generation of high antibody titers.

Example 7

Preparation of Tetanus Vaccine

Similar to example 6, tetanus vaccines where created using tetanus toxoid instead of diphtheria toxoid. Similarly, even when using very low amounts of macro-aggregated cytokines, antibody titers were significantly increased.

Example 8

Preparation of Hepatitis B Vaccines

IL-2 macro-aggregates adsorbed on alum were prepared according to example 1.

1 μg hepatitis B surface antigen (HBsAg) adsorbed to 10 μg alum was used per vaccination dose. The vaccine further comprised either no or 10 μg alum-adsorbed IL-2 macro-aggregates. Balb/cJRj female mice of 5-6 months of age were injected sub-cutaneous with the vaccines. Sera were collected 33 days after primary injection and 14 days after secondary injection. Antibody titers were tested in indirect ELISA. For this purpose, 100 μl samples of serial dilutions of the individual sera were applied to HBsAg-coated wells of ELISA plates (0.1 μg HBsAg in 100 μl coating buffer per well). Binding of antibodies was determined by applying POD-labeled secondary goat-anti-mouse IgG (Fcγ) antibodies. After the addition of the POD substrate the $OD_{450}$ was determined for several dilutions of the antisera. Binding titers were defined as the dilution at which the optical density at 450 nm reached 1.0.

33 days after primary injection, the group receiving the HBsAg vaccine without depot-adsorbed cytokines contained 1 high responder (median titer=300) and 7 non-responders (median titer=0). In contrast, the group that received HBsAg with 10 μg alum-adsorbed IL-2 macro-aggregates consisted of 4 high responders (median titer of 1500), 3 low responders (median titer of 60) and 1 non-responder (median titer=0).

14 days after the second injection, the HBsAg vaccine led to 5 high responders (median titer of 1500), 2 low responders (median titer of 20) and 1 non-responder (median titer of 0). The group vaccinated with the composition of the invention (HBsAg and 10 μg alum-adsorbed IL-2 macro-aggregates) consisted of 7 high responders (median titer of 3810) and 1 non-responder (median titer=0).

Thus, not only did the compositions of the present invention lead to higher antibody titers, they also generated earlier responses. Already 33 days after a single injection, the group receiving the vaccine with depot-adsorbed cytokine macro-aggregates had a similar antibody profile as the group that received a double dosage of the standard vaccine.

In addition, a vaccine was prepared with IL-2 adsorbed to alum, wherein the IL-2 was present as micro-aggregates instead of macro-aggregates. Thereto, recombinant IL-2 (Proleukin) was diluted in an SDS-containing buffer to prevent the formation of macro-aggregates. A vaccine dose thus contained 1 μg HBsAg, 10 μg alum-adsorbed IL-2, dissolved in a buffer containing 160 μg SDS per mg IL-2, i.e. corresponding to the Proleukin buffer solution. This group performed worse than the group vaccinated with the standard vaccine (HBsAg).

Example 9

Hepatitis B Vaccines for Intermediate and Non-responders

Similar to example 8, different HBsAg vaccines were prepared. The standard vaccine contained 1 μg HBsAg adsorbed to 10 μg Alum. Other vaccines further contained:

- 10 μg alum
- 10 μg macro-aggregated IL-2 adsorbed to 10 μg alum
- 3 μg of macro-aggregated GM-CSF adsorbed to 10 μg alum
- 10 μg macro-aggregated IL-2 adsorbed to 10 μg alum+3 μg of macro-aggregated GM-CSF adsorbed to 10 μg alum Mice of three different mouse strains were vaccinated with the vaccines. Balb-c mice are high-responders, C57Bl/6 mice are intermediate responders, while SJL are non-responders. Sera were collected xxx days after injection and titers were determined as in example 8.

TABLE 2

| Median HBsAg antibody titers per group | | | |
|---|---|---|---|
| | Balb-c (high resp.) | C57Bl/6 (int. resp.) | SJL (non-resp.) |
| HBsAg | 350 | 150 | 100 |
| HBsAg + AL | 1300 | 780 | 30 |
| HBsAg + IL-2/AL | 4000 | 9000 | 2000 |
| HBsAg + GM-CSF/AL | 4800 | 1700 | 600 |
| HBsAg + GM-CSF/AL + IL-2/AL | 37000 | 16000 | 1600 |

Thus, addition of alum-adsorbed IL-2 or GM-CSF macro-aggregates leads to higher antibody titers. Furthermore, the combination of IL-2 and GM-CSF macro-aggregates leads to an even better immunization. Remarkably, good antibody titers are obtained in non-respondent mice when using the compositions of the present invention. When using HBsAg in combination with alum-adsorbed macro-aggregated cytokines, non-respondent mice show higher antibody titers than high-respondent mice that are vaccinated with the standard vaccine.

Example 10

Hepatitis B Memory Recall

Hepatitis B vaccines were prepared according to example 8 and contained either 10 µg alum or 10 µg alum whereto 10 µg macro-aggregated IL-2 was adsorbed. Mice were vaccinated by intraperitoneal injection at 0, 4 and 8 weeks. In addition, separate experiments were performed in the same manner, except that injections were performed intramuscular, subcutaneously or intradermal.

139 days after the last injection, the mice were challenged with 1.0 μg soluble HBsAg (i.e. without alum or IL-2). This aims to mimic a naturally occurring hepatitis B infection, which would provoke an immune response in a vaccinated animal. Antibody titers were determined as in example 8, before the challenge with soluble HBsAG and 14 days thereafter. The results for the intraperitoneal challenge injection experiment are shown in FIG. 10. As can be seen, the challenge results in increased antibody titers in mice vaccinated with the "standard" vaccine (not containing macro-aggregated cytokines). Indeed, in this group (1) antibody titers are higher after challenge (aC) than before challenge (bC). However, titers are much further increased in mice that have been vaccinated with the vaccine according to the invention (group 2). Similar observations have been made for mice vaccinated intramuscular, subcutaneous or intradermal.

Example 11

Size Distribution of Cytokine Macro-aggregates

As in example 1 above, in the present experiment IL-2 (Proleukin) from Novartis was used.

1 mg of IL-2 was contained lyophilized in an injection ampoule.

The lyophylizate contained, besides 1.0 mg of IL-2, buffer substances and SDS (0.160 μg SDS per mg of IL-2). The lyophylizate was dissolved by injection of 1.0 ml of sterile, 25 nm filtered water. The clear solution was removed from the injection ampoule and diluted with 5 ml of sterile 25 nm filtered phosphate buffered saline (PBS).

Immediately after dilution a sample was filled into a cuvette and placed in a Zetasizer nano ZF machine. Light scattering was determined at wave length 633 nm at time points 0 h, 1 h, 2 h, 3 h, and 4 h. Light scattering intensity was plotted against particle size from 1 nm to 10,000 nm.

The results shown in FIGS. 11A-E provide:

at time point 0 h: the IL-2 is present in the solution as a mixture of mainly 20 nm large nano aggregates. In addition, some 80 nm particles and few 300 nm particles are seen. Based on an area under the curve analysis, this first peak of mainly 20 nm large particles (range of about 10 to 40 nm) represent about 65% of the material, wherein the larger 80 nm particles peak (range of about 40 to 100 nm) represents about 25% and the remaining peak of 300 nm particles (range of about 200 to 450 nm) represent about 10%. In other words, from the onset and in the absence of SDS already more than 25% of the IL2 is present in the macro-aggregate form.

After 1 h most of the particles were present as 110 nm particles. In said instance the 20 nm peak has completely disappeared and no particles below 15 nm could be found. In addition only few 20 nm particles were found. Based on an area under the curve analysis, this first peak of mainly 20 nm particles only represents about 6.5% of the material.

During the further course of the experiment the size of the particles only further increased:

- after 2 h a peak of 80 nm and a peak of 200 nm particles, with no particles below 60 nm and the trailing peak representing about 17% of the material.
- after 3 h a peak of 200 nm and a peak of 700 nm particles, with no particles below 100 nm.
- after 4 h a peak of 200 nm and a peak of 1100 nm particles, with no particles below 150 nm;
- after 5 h a peak of 500 nm and a peak of 3000 nm particles (data not shown)

Example 12

Influence of Particle Size on Antibody Titers

In this experiments we investigated the effect of the particle size on antibody titers in a vaccination setup. Particle size of the cytokine aggregates was controlled by the presence or absence of SDS in the preparation of the vaccine, in the present instance using the Hepatitis B virus antigen (HBsAg).

The experiment was done as follows:

each mouse was injected with 1.0 μg of HBsAg adsorbed to 10 μg of alum mixed with 10 μg of rhuIL-2 adsorbed to 10 μg of alum, wherein in the control group the rhuIL-2 adsorbed to 10 μg of alum was prepared in the absence of SDS with the formation of the macro-aggregates of the present invention, and in the experimental group the rhuIL-2 adsorbed to 10 μg of alum was prepared in the presence of SDS to maintain the micro-aggregates.

For the experimental group the IL-2-alum adjuvant was prepared as follows: IL-2 (Proleukin) from Novartis was obtained as a lyophilyzate in an injection ampoule.

The lyophilyzate contained, besides the rhuIL-2, all the buffer substances needed.

In order to limit aggregation 160 μg of SDS per mg of IL-2 were contained in the lyophilysate.

The lyophilyzate was dissolved by injection of 1.0 ml of sterile water into the injection ampoule.

Then the solution was removed from the injection ampoule and diluted 5 fold.

For the experimental group the PBS used for dilution contained 180 μg/ml SDS.

For the control groups PBS without SDS was used.

After several hours a suspension of alum was added in the required concentration/density.

The PBS without SDS containing IL-2 solution developed turbidity within a very short time. The PBS with SDS containing IL-2 solution did not develop turbidity.

preparation of the vaccine:

the alum containing solution and the IL-2-containing solution were mixed and incubated on a roller for one hour. The thus obtained vaccines were injected subcutaneously or intramuscularly into BALB/c mice.

After three weeks the mice were boosted with the same vaccine following the same procedure.

From the blood obtained by puncture of the retro-orbital plexus serum was prepared.

Antibody titers were determined by indirect ELISA with Peroxidase-labeled goat anti mouse IgG (Fc-specific) antibodies.

Antibody titers were defined as the dilution at which an optical density at 450 nm of 1.0 was obtained.

For each group the antibody titers and the mean were plotted As can be clearly seen in FIG. 12, antibodies obtained in mice after immunization with a vaccine that contained SDS were significantly lower than antibody titers obtained from mice that had been vaccinated with the "normal", not SDS containing vaccine.

The invention claimed is:

1. A composition comprising cytokines and sodium dodecyl sulfate, wherein said cytokines are present in cytokine macro-aggregates with an average diameter of at least 50 nm and comprising between about 33 µg to less than 95 µg of sodium dodecyl sulfate per mg of cytokine, and wherein said cytokine macro-aggregates are either:
adsorbed to a depot material; and/or
encapsulated in liposomes.

2. The composition of claim 1, comprising one or a plurality of different cytokines in macro-aggregated form.

3. The composition of claim 1, wherein said cytokines are independently selected from the group consisting of IL-2, IL-4, IL-12, GM-CSF, and IFN-alpha.

4. The composition of claim 1, wherein at least one cytokine is IL-2.

5. The composition of claim 1, wherein said depot material is aluminum hydroxide.

6. The composition of claim 1, further comprising antigenic material.

7. The composition of claim 6, wherein the antigenic material is selected from the group consisting of irradiated autologous tumor cells, irradiated allogeneic tumor cells, irradiated xenogeneic tumor cells, tumor cell homogenates, tumor cell extracts, individual tumor antigens (natural or recombinant), mixtures of tumor antigens (natural or recombinant), peptides of tumor antigens (natural or recombinant).

8. The composition of claim 6, wherein the antigenic material is microbial and/or parasitic antigenic material.

9. The composition of claim 1, further comprising one or more pharmaceutically acceptable excipients and optionally an additional pharmaceutical ingredient.

10. The composition of claim 1, wherein said liposomes are dimyristoylphosphatidylcholine (DMPC) liposomes.

11. The composition of claim 1, wherein the cytokine macro-aggregates comprise a dot-like formation.

12. The composition of claim 11, wherein the cytokine macro-aggregates are between approximately 50 nm and 6000 nm.

13. A vaccine composition comprising an effective amount of the composition of claim 1.

14. The composition of claim 1, for use as a medicament.

15. A process for preparing the composition according to claim 1, the process comprising: a) providing a mixture comprising cytokines and an aggregation-preventing agent that is sodium dodecyl sulfate; b) diluting the concentration of the sodium dodecyl sulfate to a concentration of between about 33 µg to less than 95 µg sodium dodecyl sulfate per mg cytokine; c) incubating the mixture for a time sufficient to allow the cytokines to form cytokine macro-aggregates with an average diameter of at least 50 nm; and then d) mixing with a depot material, and/or encapsulating said cytokine macro-aggregates in liposomes.

16. The process of claim 15, wherein the mixture includes antigenic material.

* * * * *